US011000542B2

(12) United States Patent
Goodall et al.

(10) Patent No.: US 11,000,542 B2
(45) Date of Patent: May 11, 2021

(54) TREATMENT AND PREVENTION OF THE COMMON COLD USING POVIDONE-IODINE

(71) Applicant: FIREBRICK PHARMA LIMITED, Melbourne (AU)

(72) Inventors: Stephen Goodall, Creswick (AU); Peter Molloy, Creswick (AU)

(73) Assignee: FIREBRICK PHARMA LIMITED, Melbourne (AU)

( * ) Notice: Subject to any disclaimer, the term of this patent is extended or adjusted under 35 U.S.C. 154(b) by 50 days.

(21) Appl. No.: 15/327,998

(22) PCT Filed: Jul. 6, 2015

(86) PCT No.: PCT/AU2015/050378
§ 371 (c)(1),
(2) Date: Jan. 20, 2017

(87) PCT Pub. No.: WO2016/011496
PCT Pub. Date: Jan. 28, 2016

(65) Prior Publication Data
US 2017/0165296 A1    Jun. 15, 2017

(30) Foreign Application Priority Data

Jul. 23, 2014  (AU) .............................. 2014206143

(51) Int. Cl.
| | | |
|---|---|---|
| *A61K 33/18* | (2006.01) | |
| *A61K 31/79* | (2006.01) | |
| *A61K 9/00* | (2006.01) | |
| *A61P 31/16* | (2006.01) | |
| *A61P 31/14* | (2006.01) | |
| *A61P 31/12* | (2006.01) | |
| *A61K 45/06* | (2006.01) | |

(52) U.S. Cl.
CPC ............ *A61K 33/18* (2013.01); *A61K 9/0043* (2013.01); *A61K 31/79* (2013.01); *A61K 45/06* (2013.01)

(58) Field of Classification Search
CPC ...... A61K 33/18; A61K 31/79; A61K 9/0043; A61P 31/12; A61P 31/14; A61P 31/16
See application file for complete search history.

(56) References Cited

U.S. PATENT DOCUMENTS

| | | | | |
|---|---|---|---|---|
| 4,523,589 A | * | 6/1985 | Krauser ................ | A61M 15/00 128/203.27 |
| 2003/0180380 A1 | | 9/2003 | Hansen | |
| 2008/0138438 A1 | * | 6/2008 | Taylor ................... | A01N 31/16 424/604 |

FOREIGN PATENT DOCUMENTS

| | | |
|---|---|---|
| CN | 103751274 A | 4/2014 |
| JP | 2004352642 A | 12/2004 |
| KR | 1020170033925 A | 3/2017 |
| KR | 101935250 B1 | 1/2019 |
| WO | 2012/177251 A1 | 12/2012 |
| WO | 2016011496 A1 | 1/2016 |

OTHER PUBLICATIONS

Mäkelä, Mika J., et al. "Viruses and bacteria in the etiology of the common cold." Journal of clinical microbiology 36.2 (1998): 539-542.*
Kramer A. et al, New Aspects of the Tolerance of the Antiseptic Povidone-Iodine in Different ex vivo Models, Dermatology, 2002, vol. 204. Supplement 1, p. 86-91.
Reimer, K., et al., "Antimicrobial Effectiveness of Povidone-Iodine and Consequences for New Application Areas", Dermatology, 2002, vol. 204, Supplement 1, pp. 114-120.
Rombaux, P., et al., "The role of nasal cavity disinfection in the bacteriology of chronic sinusities", Rhinology, Jun. 2005, vol. 43, No. 2, pp. 125-129.
Chepla K. et al, Interstitial Pneumonitis After Betadine Aspiration, The journal of Craniofacial Surgery, 2012, vol. 23 (6), p. 1787-1789.
Wutzler P et al.: "Virucidal Activity and cytotoxicity of the liposomal formulation of Povidone-iodine", Antiviral Research, Elsevier BV, NL, vol. 54, Jan. 1, 2002 (Jan. 1, 2002), pp. 89-97, XP002248381, ISSN: 0166-3542, DOI: 10.1016/S0166-3542(01)00213-3.
International Search Report for Application No. PCT/AU2020/050586; dated Aug. 14, 2020; pp. 1-5; Woden, Australia.
Written Opinion of the International Searching Authority for Application No. PCT/AU2020/050586; dated Aug. 14, 2020; pp. 1-5; Woden, Australia.

* cited by examiner

Primary Examiner — Bethany P Barham
Assistant Examiner — Peter Anthopolos
(74) Attorney, Agent, or Firm — Rimôn, P.C.

(57) ABSTRACT

The present invention provides a method of treating and preventing the common cold and associated secondary illnesses in a human subject, when the common cold is caused by viruses. The method comprises applying to the nasal passages of the human subject at ambient temperature, an effective amount of a pharmaceutical preparation comprising povidone-iodine (PVP-I) at a concentration of greater than 0.10% w/v and less than 2.5% in which at least 50% of the PVP-I is not associated with liposomes or other particulate carriers.

19 Claims, 7 Drawing Sheets

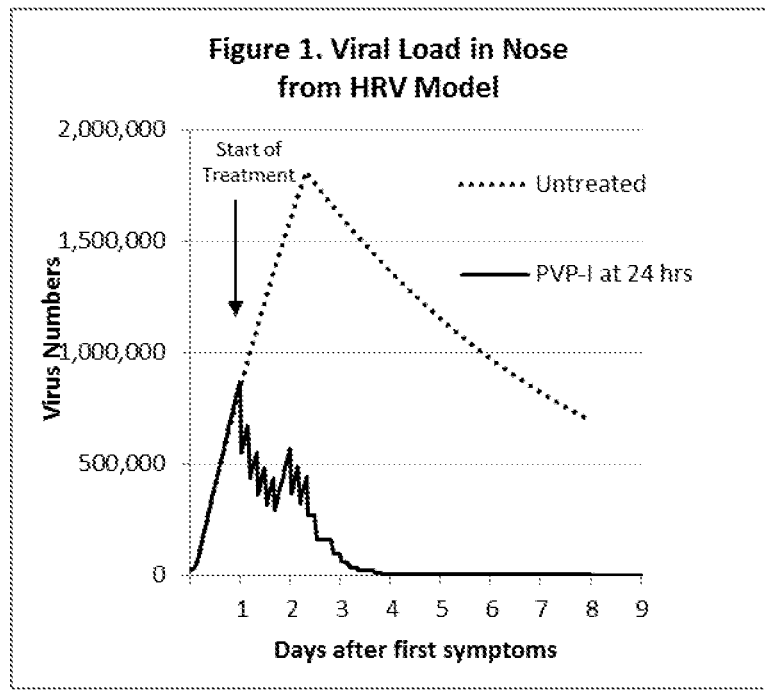
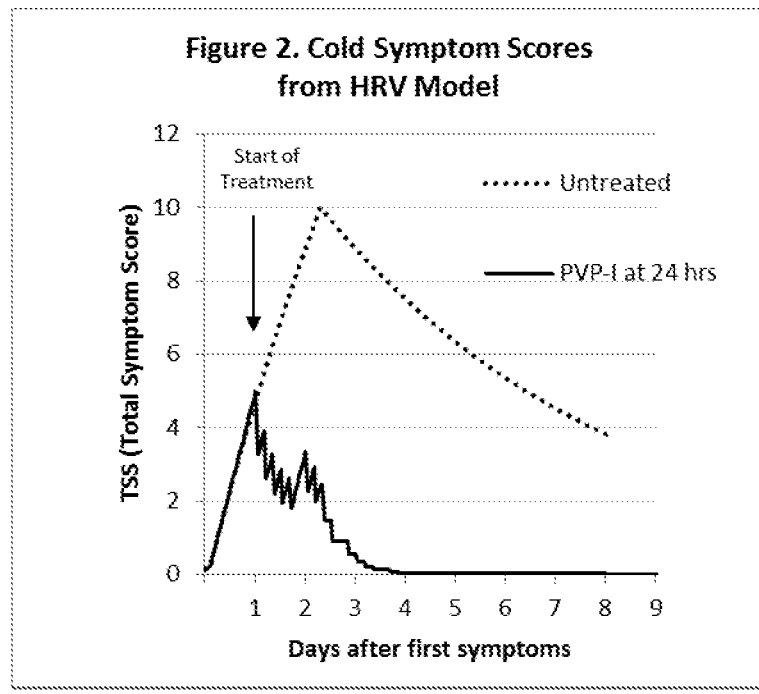

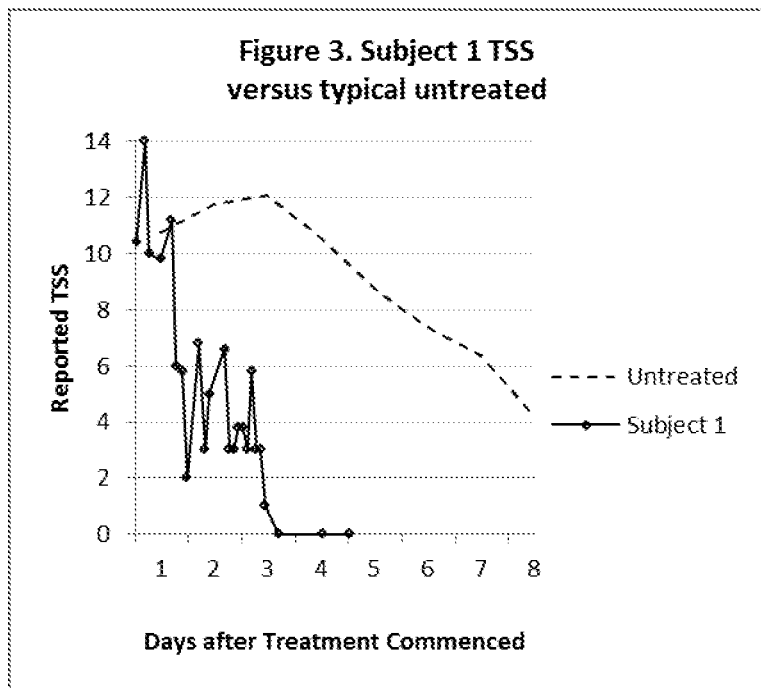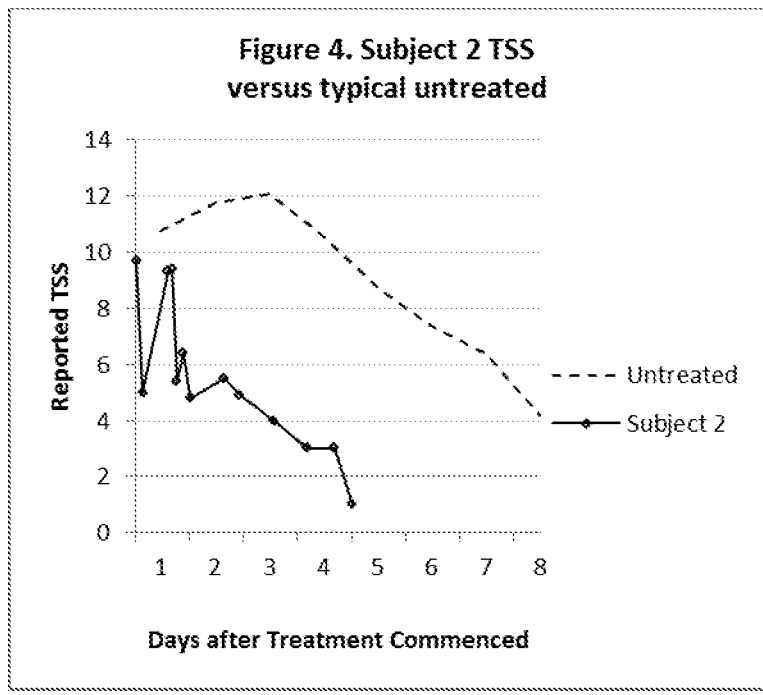

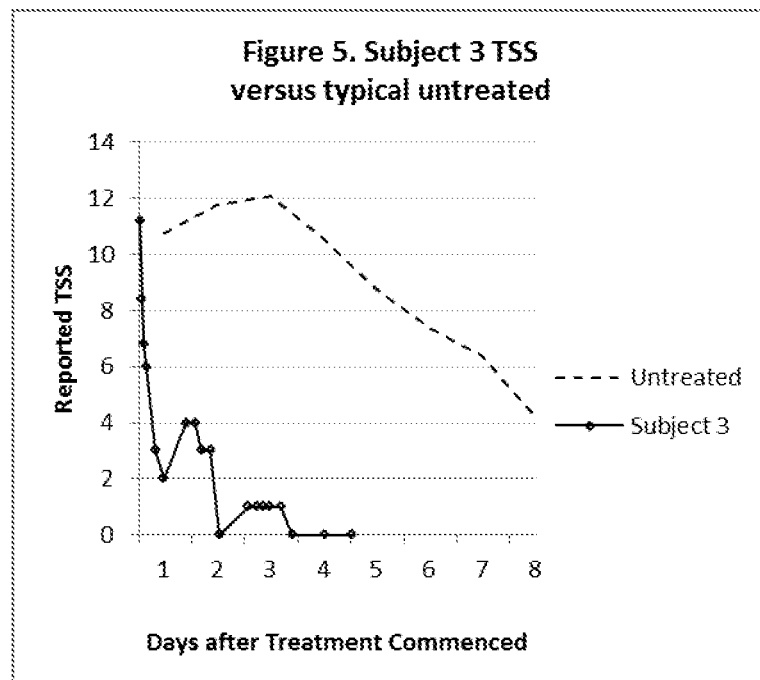
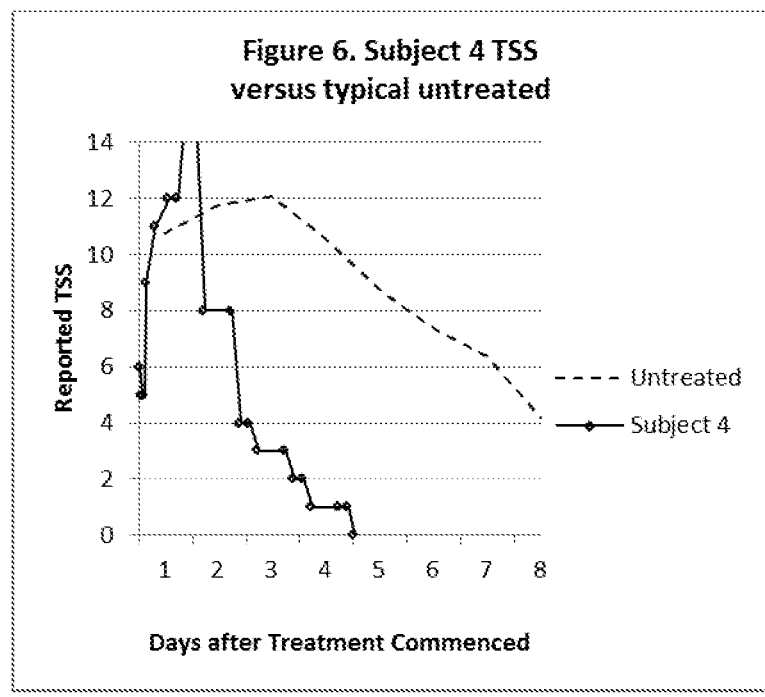

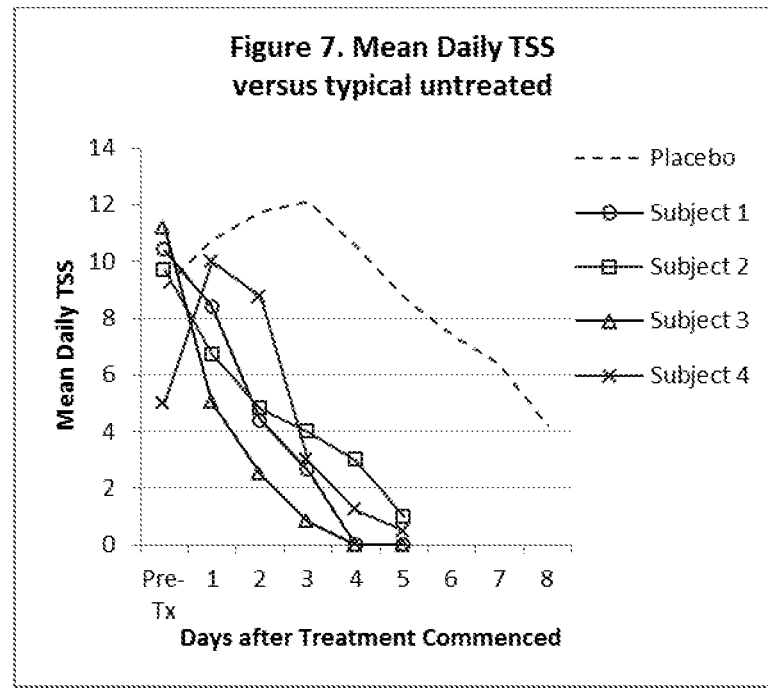
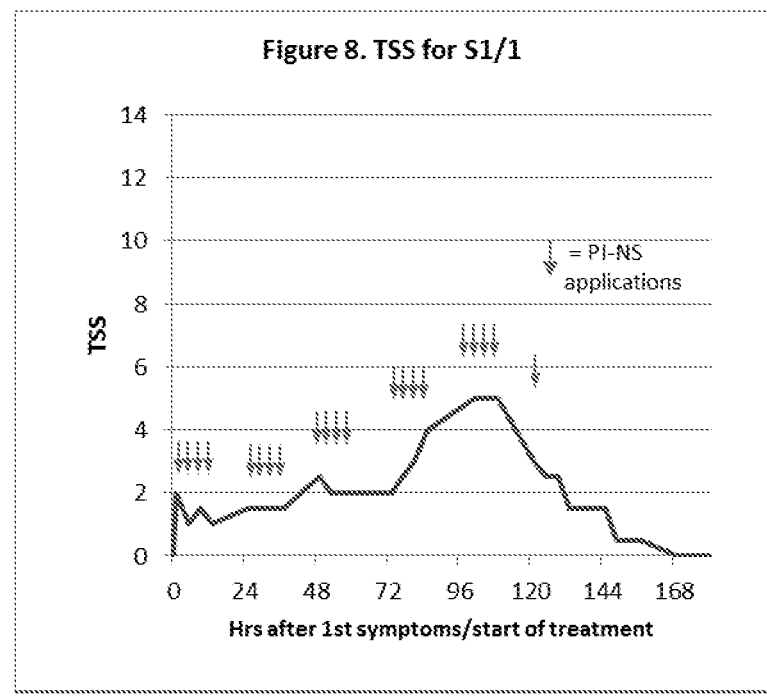

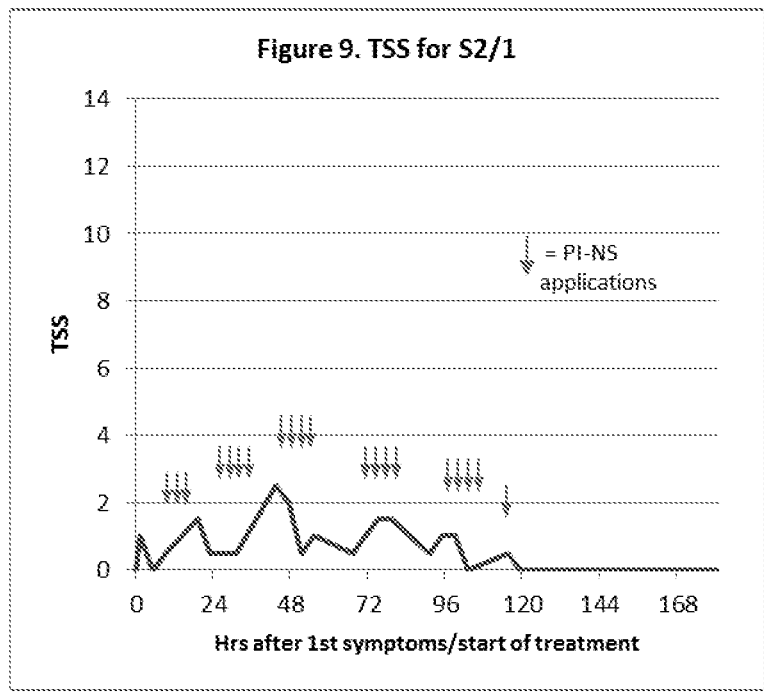
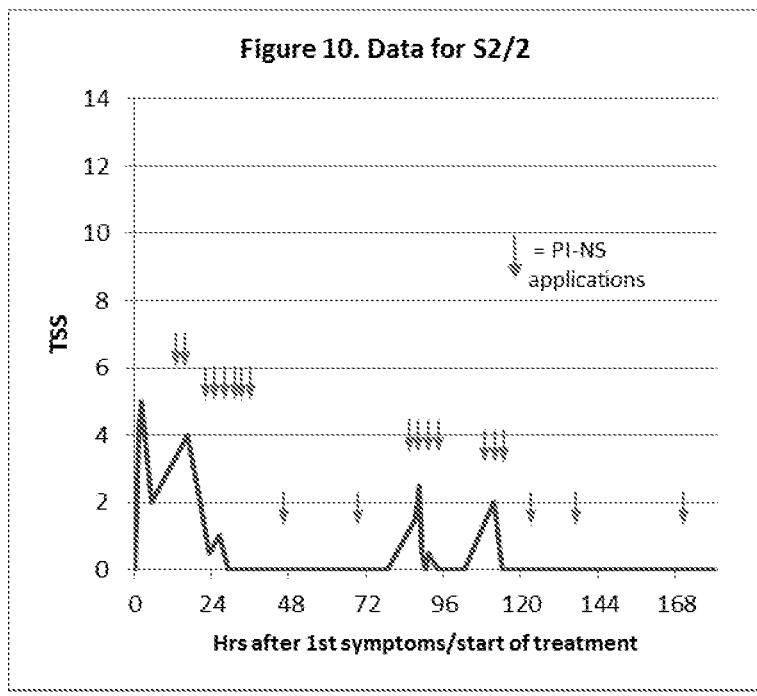

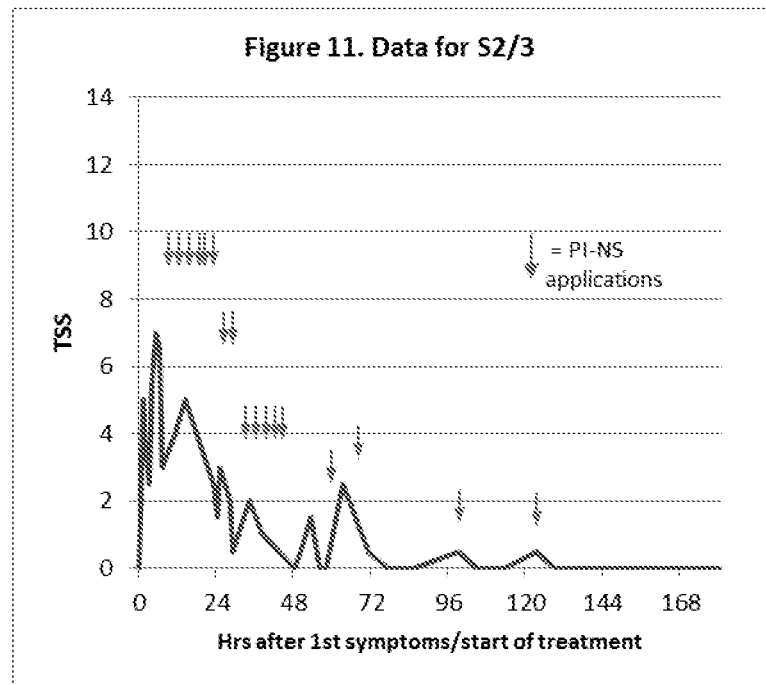
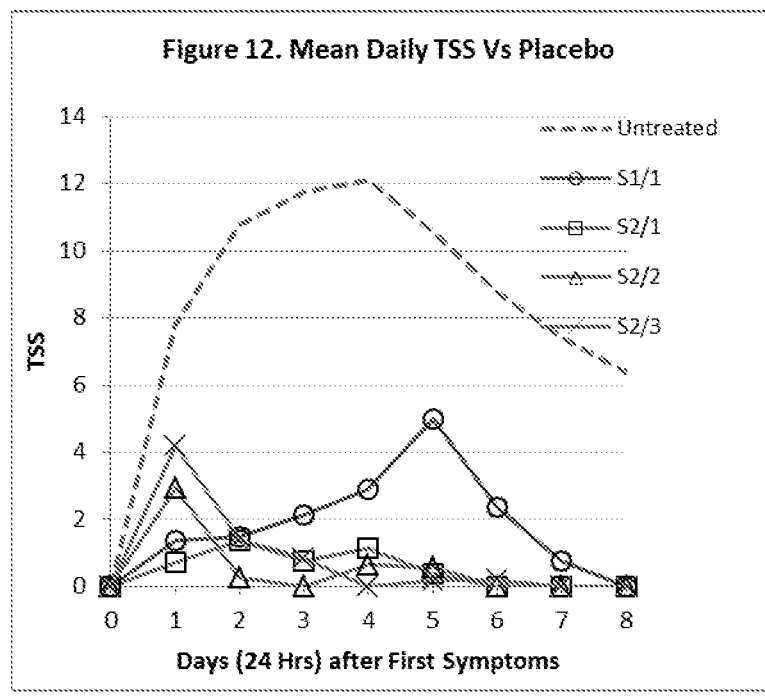

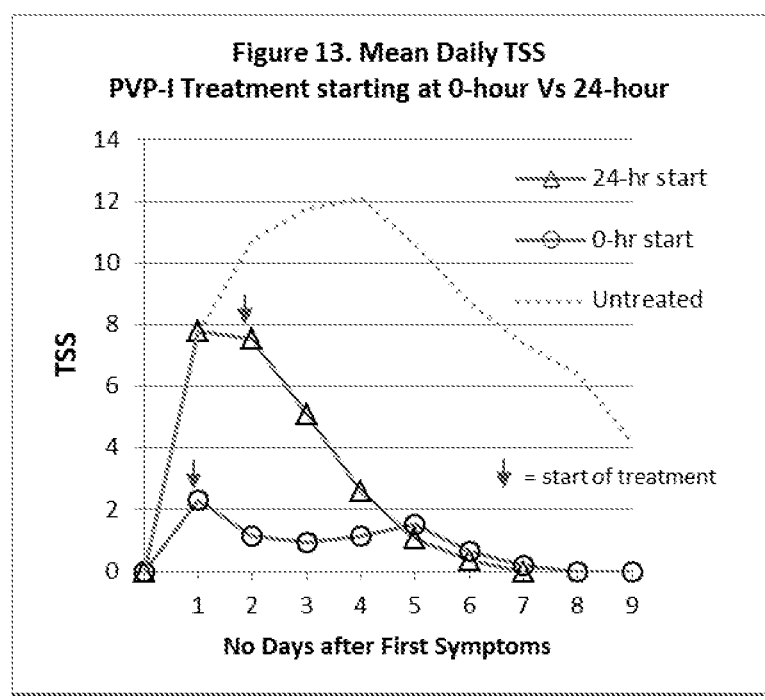

TREATMENT AND PREVENTION OF THE COMMON COLD USING POVIDONE-IODINE

CROSS-REFERENCE TO RELATED APPLICATIONS

This application claims priority to PCT Application No. PCT/AU2015/050378, filed Jul. 6, 2015, and Australian Application No. 201406143, filed Jul. 23, 2014. Each of these applications is incorporated herein by reference in its entirety.

FIELD OF THE INVENTION

This invention is directed to methods for treatment and prevention of the common cold and its sequelae using topical preparations comprising the broad-spectrum antimicrobial agent povidone-iodine.

BACKGROUND OF THE INVENTION

Infective respiratory diseases are often broadly classified into upper respiratory tract infections (URI) and lower respiratory tract infections (LRI). The upper respiratory tract includes the oral cavity, nasal cavity, sinuses, middle ear, pharynx and larynx. The lower respiratory tract includes the trachea, bronchi, bronchioles and alveoli in the lungs. Each site can be the locus of a specific clinical condition that may have discrete presentation, causation and therapeutic challenges. For this reason, it is not appropriate to talk about "upper respiratory infections" or "lower respiratory tract infections" as single, continuous or homogeneous conditions or therapeutic targets, because each term embraces a multiplicity of clinically discrete sites, causations, clinical conditions and treatment challenges. Further, it would not be assumed in the art that any treatment disclosed as useful for a specific site or condition would necessarily indicate its utility in another site or condition in the upper or lower respiratory tract.

The common cold is a widely-recognised URI, usually but not exclusively due to a viral infection of the nasal mucosa. Other common URI include tonsillitis, sinusitis and otitis media. Acute tonsillitis is an infection of the palatine tonsils in the pharynx that is typically caused by bacteria belonging to the group A streptococcus genus, and is commonly treated with penicillin. Sinusitis is an inflammatory condition of the sinuses that can be due to infection, allergy or auto-immune causes; where a bacterial cause is suspected, it is generally treated with an antibiotic. Otitis media is an infection of the middle ear often caused by bacteria and typically treated with antibiotics. Unlike these three cited conditions, currently, there is no effective treatment for the common cold, which is generally caused by viruses.

While normally mild and self-limiting, the common cold, or simply the "cold" as it is generally known, has a very high incidence and prevalence and causes high morbidity, medical costs and productivity losses, as well as contributing to an unduly high burden on the health care system. In the United States, adults experience an average of 2 to 3 colds per year, while school children can have more than 10 a year, in total contributing to an estimated 1 billion colds each year, resulting in up to 100 million doctor visits per year that cost the community an estimated $8 billion and add considerably to the burden on the medical system, which in most advanced economies is already over-stretched. In addition, up to 200 million school days are missed annually and 150 million workdays are lost due to employees having colds, and up to another 150 million workdays lost due to parents staying home to care for their sick children with colds. The total economic impact of cold-related productivity losses has been estimated to potentially exceed $20 billion per year in the United States alone, with losses of comparable scale in other industrialized countries. Additionally, billions of dollars in the United States are spent each year on over-the-counter (OTC) medicines, supplements and other remedies that mostly have little or no proven benefit, other some modest symptomatic relief.

In addition, there is the indirect cost of antibiotic resistance caused in part by over-prescribing of antibiotics for colds by primary care physicians, despite the fact that most colds are viral in origin and antibiotics only target bacteria. This is becoming an extremely serious medical problem because of the rise of drug-resistant pathogenic bacteria.

A further problem is that colds may predispose or precipitate other conditions, notably otitis media, sinusitis and bronchitis, resulting in additional morbidity, medical cost, productivity losses and antibiotic use.

In addition, for certain "at-risk" individuals, colds can lead to serious lower respiratory infections such as pneumonia, due to enhanced susceptibility of the individuals or as a result of exacerbation of an underlying respiratory disease. These at-risk individuals include people undergoing cancer chemotherapy or who are otherwise immune-compromised, and people with underlying respiratory disease including asthma, Chronic Obstructive Pulmonary Disease (COPD), cystic fibrosis and emphysema. In such at-risk individuals, a cold can represent a serious threat that could lead to hospitalisation and potentially be life-threatening.

Despite all these important medical, economic and societal needs for an effective treatment or preventative for the common cold and despite decades of medical research in the field, there is no effective treatment available for colds and no vaccine exists to prevent colds. The reasons for this and the ongoing challenges are discussed below.

The common cold is a symptom complex initiated by an infection of the nasal mucosal cells inside the nasal cavity. For the purposes of the present invention, the term "nasal passages" will be used to include all those sites within the nasal cavity and oropharynx that are the typical site of the infection that causes the common cold symptom complex. While a cold can cause or predispose other URI or LRI notably sinusitis, otitis media and bronchitis, these are regarded in the art and defined herein as secondary complications or sequelae of a cold and not part of the common cold condition itself.

Overwhelmingly, viruses are the cause of the infection of the nasal passages leading to the condition known as the common cold. Indeed, identified and characterised viruses are known to cause at least 70% of all colds, while a further approximately 25% of colds are non-specific with respect to cause, but are believed to be viral, although in such cases the specific viral cause has not been identified or characterised. Of the viruses known to cause colds, the most common is the human rhinovirus (HRV), which is believed to account for at least half of all colds and therefore the majority of viral colds. However, there are more than 100 serotypes of HRV. In addition, there are many other viruses that can cause colds including coronaviruses, influenza viruses, parainfluenza viruses and respiratory syncytial virus (RSV). In many cases, there are numerous strains or serotypes of each. Overall, an estimated 200 species, strains or serotypes of viruses can cause the infection of the nasal passages that leads to the common cold.

Despite the range of potential infective causes, the symptoms of the clinical condition that results from the infection are generally similar. Symptoms may include sneezing, rhinorrhoea (runny nose), nasal congestion, sore throat, coughing, headache, malaise, chills and myalgia (body aches and pains). It is the constellation of these symptoms or the "symptom complex" that defines the condition generally known as the common cold rather than the infection per se. Indeed, some infected individuals will present with no symptoms, i.e. have no cold, even when they can be shown microbiologically to have an infection of the nasal passages. One reason for the idiosyncrasy is that the symptom complex is the result of the body's reaction to the infection rather than the infection itself.

The common cold starts as an infection of the cells lining the nasal passages. Because most of the research in the field has focused on HRV, the clinical pathology of HRV colds has been much better characterized than other viral colds, although it is generally assumed that the pathology would be similar for most viral colds. For HRV colds, once a cell is infected, the viruses multiply rapidly inside the cells and after 8-10 hours cause the cell to burst and release large numbers of infectious progeny viruses into the nasal passages that can infect other cells to propagate the infection.

The cell damage caused by the infection triggers local cellular defence mechanisms, including the release of the chemical bradykinin that is believed to directly cause sneezing, rhinorrhoea, congestion, sore throat and cough. These are known as the "local symptoms" of the common cold.

In addition to these non-specific cellular defences, certain immune cells present in the nasal passages, particularly monocytes and granulocytes, become engaged. Monocytes detect the presence of viral antigens or nucleic acid, typically RNA, and release cytokines, which are pro-inflammatory chemicals that recruit other immune cells, notably granulocytes, to the site of the infection or foreign material. Granulocytes, especially neutrophils in the case of colds, ingest and destroy foreign material including invading microorganisms. They also secrete more cytokines to attract even more neutrophils to the site to accelerate virus removal. However, as a side effect, the cytokines cause a low grade fever, drowsiness, malaise, myalgia and headache. These are known as the "systemic symptoms" of a cold, but are not unique to colds and can occur to some extent whenever the immune system reacts to foreign proteins or nucleic acid, for example following a vaccination or as a result of a bacterial or viral infection anywhere in the body.

The constellation of these local and systemic symptoms represents a "symptom complex" that is characteristic of and defines the clinical condition known as a cold. The composition, severity and timing of the common cold symptom complex may vary from one individual to another, depending on their underlying health status and pre-existing conditions, such as immunodeficiency or asthma. It may also vary from one infecting virus to another. The diverse range of viral causes and the range of impacts, from the comparatively mild through to serious and in some instances fatal consequences of such infections, have presented major challenges for antiviral drug development in the field.

Once a subject is infected, cold symptoms start to appear 24-36 hours after the initial infection in the nasal passages and typically last 8-9 days from the time of onset. During the first 4-5 days of the cold, large numbers of the infectious virus are produced and can be detected in the nasal mucous, which is thought to be the principal vehicle for transmission of the disease. Transmission occurs either through aerosolisation during coughing and sneezing or by nose-blowing with other people then breathing in the virus-laden aerosol particles or touching contaminated hands or surfaces. The substantial amount of nasal mucous produced during the first few days of the cold amplifies viral shedding from infected individuals and thereby the efficiency of the transmission process. Further, research has shown that even after all symptoms have disappeared, viral shedding from a cold may continue at a low level for a further 2-3 weeks.

Unlike many viral diseases, there is no vaccine for the common cold. Viral vaccines rely on the long-term immune memory of a particular virus, so that when that virus re-presents, antibodies already exist to immediately target the virus for destruction by various immune processes before it can cause an infection. However, the immunity derived from an infection by one cold virus may be relatively short lived and restricted to only one particular virus or serotype, whereas colds can be caused by up to 200 different viruses that are constantly evolving and thereby evading the antibody-mediated immune system. Thus, antibody-mediated immunity plays little practical or effective role in preventing the common cold in the population.

The alternative to prevention with a vaccine is treatment subsequent to the infection, but there are several substantial challenges to treating a cold. One of these is that there are many microorganisms that can cause a cold. In contrast, other infectious diseases typically have a single microbial cause and an uncomplicated cause-symptom pathway. Examples are human immunodeficiency virus (HIV) that causes AIDS and herpes simplex virus (HSV) that causes cold sores. In each case, specific antiviral treatments are available that suppress or destroy the virus responsible and thereby treat the symptoms of the disease. The common cold is different to these diseases, because it can be the result of an infection by any one of at least 200 different microorganisms.

Numerous attempts over many years have been made to develop antiviral agents as possible treatments for the common cold, but none has succeeded in reaching the market. Human rhinovirus (HRV) is the primary causative agent of the common cold and has been the focus of almost all antiviral drug development in the field. It is now known that there are three HRV species, A, B and C, which fall within the genus Enterovirus (EV) and the family Picornaviridae. HRV species are further divided into over a hundred distinct serotypes. Virtually all modern drug discovery and development aimed at the common cold took place between the 1980s and the early 2000s and with few exceptions was aimed at developing drugs that targeted HRV specifically. At one time or other during this period, most of the major pharmaceutical companies attempted to develop antiviral drugs targeting HRV, but by 2000 most programs had been mothballed or abandoned. One exception was the drug pleconaril, which was still under development at the US company, Viropharma, during the early 2000s. Pleconaril belongs to the capsid binder class of antiviral agents and binds to the coat or capsid of the virus to interfere with uncoating, which is an early, essential stage in the infectious cycle. Other capsid binders have been reported to interfere with the binding of HRV to the ICAM-1 receptor on cells, also preventing entry of the virus into cells. Viropharma's 2002 New Drug Application (NDA) received a unanimous vote against approval by the FDA Advisory Committee because Phase III data indicated only a one-day reduction in cold duration while presenting a risk of cytochrome P450 induction leading to possible undesirable side effects. Viropharma abandoned pleconaril and no other antiviral drug for HRV has since progressed to a Phase III trial.

Apart from side effects, another limitation of HRV-specific antiviral agents is that they only target around half of all colds, at best. This narrow spectrum problem for antiviral drugs is a particular concern because it may not be possible for physicians to distinguish the causative organism based on the symptom complex presentation alone. Another limitation is that because they target specific receptor or protein binding mechanisms, viruses can mutate and become resistant to the agent, rendering the agent ineffective.

In addition to these HRV-specific approaches, a small number of non-specific approaches have been tested clinically, including interferon (a chemical produced naturally by cells to defend against virus infection), acidic buffers (because some viruses, especially HRV, are acid labile), and carrageenan (a seaweed extract). Interferon was shown to be ineffective and acidic buffers reduced viral shedding but had little impact on symptoms. Only carrageenan has been developed commercially and introduced in a small number of countries, but it is not approved in other countries including the US. The putative mechanism by which it works is to coat viruses and nasal surfaces with a polysaccharide that prevents attachment of the virus. Clinical studies with carrageenan have shown mixed results, but it appears that if used continuously during the symptomatic period of a cold it may slightly reduce the duration of a cold, but may have little effect on the severity of the symptoms.

Another challenge for any treatment for the common cold is that the intervention window is very narrow. Once symptoms are observed, the infection may have been in progress for 24-36 hours and thereafter, by day 3 or 4 after first symptoms, the viral load in the nasal mucous is already reduced to relatively low levels. This means that any therapeutic intervention targeting the virus would have a limited window of time in which to exert its effect and achieve significant symptomatic benefits or effect in terms of reduction of cold duration. This presents a practical problem for any drug that is available on prescription, because of the additional delay in obtaining access to the drug once symptoms are observed.

Further as already noted, the symptom complex is a product of the body's reaction to the infection, rather than the infection per se. Once primed by the infection, the cellular defence mechanisms and immune response can remain engaged and are known to cause ongoing symptoms for several days even after the amount of virus in the nasal passages starts to decline. This limits the capacity of an antiviral agent to treat cold symptoms based on its antiviral action alone.

In summary, there are formidable technical challenges to discovering and developing an effective treatment and as a result, and despite decades of research into possible treatments, no effective treatment has emerged despite a very substantial medical, economic and social need to find, develop and commercialise an effective treatment for the common cold.

An effective treatment for the cold is generally considered in the art to be one that demonstrates a significant reduction in (1) the severity of symptoms, and/or (2) the duration of a cold. For the purposes of evaluating symptom severity effects, those in the art commonly employ a measure referred to as the total symptom score (TSS), which is a measure of the severity of the overall symptom complex based on an un-weighted composite of selected symptoms, typically calculated as a daily mean score. The TSS is commonly comprised of five local and three systemic symptoms, each assessed on an ordinal severity scale. The duration of a cold is another important measure for clinical evaluations. One measure considered to be valid in the art is the time to alleviation of illness (TAI) which is determined as the time from initiation of treatment to the time when rhinorrhoea is absent and no other individual symptom is rated above 'mild' in severity.

In addition to these symptom-related measures, in studies where subjects are deliberately infected with a cold virus, typically HRV, it is possible to measure the viral load present at various times after infection as another important measure of the effectiveness of any intervention in the common cold. This is commonly done by sampling the mucous in the nasal passages, using swabs or nasal washings, and detecting the amount or concentration of virus present using techniques such as cell culture or quantitative polymerase chain reaction (qPCR).

Other potentially important clinical endpoints in the evaluation of any cold therapy include the extent to which it (1) reduces the incidence or severity of secondary illnesses such as otitis media, sinusitis and bronchitis, (2) reduces the incidence or severity of serious LRI and disease exacerbations in at-risk individuals, and (3) prevents a cold occurring when a subject is exposed to others with colds.

Topical treatment of colds by applying broad-spectrum chemical disinfectant-type agents to the nasal passages has not been attempted in the field of respiratory diseases management. Such an approach may seem to have potential superficially, because of the ability of the disinfectant to eradicate the virus directly from the nasal passages. However, in most cases there are serious limitations with such agents including local burning, irritation, cellular toxicity, systemic toxicity and unpleasant odour. One chemical disinfectant that has reduced toxic potential and recently has been shown to be safe to use in the nose is povidone-iodine, commonly referred to as PVP-I.

Povidone-iodine (PVP-I) is a broad-spectrum topical microbicide that is known to rapidly inactivate viruses, principally through the potent oxidative effects of free iodine on microbial proteins and nucleic acids. It is known in the art that the instantaneous potency of any PVP-I solution is related to the concentration of free iodine released from the polymer carrier, where free iodine is typically less than 30 ppm in PVP-I solutions, ensuring adequate potency for antimicrobial action while avoiding the iodine-related stinging, burning and other toxicities of traditional iodine solutions such as Lugol's solution, which is a solution of free iodine in potassium iodide. With a PVP-I solution, the majority of the iodine remains within or bound to the complex and is only released as the exogenous free iodine is depleted, for instance as a result of its oxidative interaction with microbial protein. In this way a relatively stable low level of free iodine is maintained while a reservoir of inactive complex-bound iodine remains close to the site of action and ready for use as needed.

Because the oxidative effect of free iodine is potent and not protein or target specific, PVP-I has shown no susceptibility to viral resistance development despite more than 30 years of extensive usage as a topical antiseptic. In addition, it has found some therapeutic utility as a topical agent to treat certain infective skin conditions, including acne and cold sores, which are caused by certain bacteria and herpes simplex virus respectively. In some markets, including Australia and Japan, it is widely used as a throat gargle to treat sore throats, many of which may be associated with the common cold. However, as shown in one randomised, controlled study by Satomura et al ("Prevention of upper respiratory tract infections by gargling: a randomized trial." American Journal of Preventive Medicine 29.4 (2005):

302-307) while such gargling practices may have a slight effect on the sore throat or pharyngeal symptoms of colds, they have no significant effect on nasal cold symptoms or bronchial complications, and no benefit in terms of reducing the incidence of the common cold.

The intranasal use of PVP-I has been extremely limited. PVP-I has been proposed as an intranasal solution or cream for eradication of antibiotic resistant bacteria, which can be inadvertently carried in the nasal passages and contribute to outbreaks of infection in the hospital setting. Hill and Casewell ("The in-vitro activity of povidone-iodine cream against Staphylococcus aureus and its bioavailability in nasal secretions." Journal of Hospital Infection 45.3 (2000): 198-205) tested a 5% PVP-I cream and concluded it may have a role in the prevention of colonization and infection caused by MRSA. Hollander et al ("Asymptomatic carriage of Klebsiella pneumoniae producing extended-spectrum b-lactamase by patients in a neurological early rehabilitation unit: Management of an outbreak." Journal of Hospital Infection 48.3 (2001): 207-213) used a 1.25% PVP-I solution as a nasal spray to eradicate drug-resistant Klebsiella pneumonia from the nasal passages of patients in a neurological rehabilitation unit. Kramer et al ("New aspects of the tolerance of the antiseptic povidone-iodine in different ex vivo models." Dermatology 204.Suppl. 1 (2002): 86-91) confirmed that PVP-I solutions were also effective against MRSA and showed that a PVP-I concentration of 1.25% or lower was suitable for use in the nose. In none of these cases was it suggested that PVP-I solutions might have utility in treating or preventing the common cold as caused by a virus.

Despite its broad-spectrum, lack of resistance potential, utility in certain therapeutic applications and potential safety and utility in the nasal passages for eradication of drug-resistant bacteria, PVP-I has significant known limitations that would lead one skilled in the art to conclude that PVP-I would not be suitable, safe or effective as an agent to treat the common cold as caused by a virus.

One perceived limitation is that PVP-I is a topical agent that does not enter nasal cells, while the replication of cold viruses occurs exclusively inside nasal cells. Those skilled in the art would conclude that any topical intervention such as PVP-I might temporarily degrade the viral load in the nasal mucous but would have no direct impact on the ongoing infection inside the cells, and the latter would continue to drive bradykinin and cytokine production and thereby the symptom complex. In any case, as infected cells burst and released more virus, the viral load in the nasal mucous would be replenished, counteracting any depletive effects of PVP-I. This contrasts with the known useful application of PVP-I to the nasal passages for eradication of bacteria such as MRSA, where the bacteria reside and replicate on the surface of the nasal cells and are not engaged in any active infection.

The process of mucociliary clearance also needs to be considered in the intranasal use of a topical agent, including PVP-I. Mucociliary clearance is a natural cleaning process in the nasal passages whereby the sweeping effect of the hairlike follicles on nasal cells, called cilia, direct mucous towards the throat allowing the mucous to exit the nasal passages and ultimately be swallowed. This process is designed to constantly clean the nasal passages by removal of contaminants including microorganisms in nasal mucous. Gluck et al ("A clinical study on the tolerability of a liposomal povidone-iodine nasal spray: implications for further development." ORL 69.2 (2006): 92-99) showed that the mucociliary clearance time was approximately 15 minutes in healthy noses and that the application of a PVP-I preparation did not significantly alter the clearance time. This would indicate that the maximum time available for a topical intranasal preparation to have any antiviral or other local effect is approximately 15 minutes.

In addition, during a cold, any topical agent is further rapidly cleared by rhinorrhoea or runny nose, which according to Winther ("Rhinovirus infections in the upper airway." Proceedings of the American Thoracic Society 8.1 (2011): 79-89) is the most common early symptom of the common cold in adults. Rhinorrhoea is due to watery fluid secretions from nasal glands and goblet cells in the nasal passages that are principally designed to expel pathogens and other noxious materials from the nose. The volume of the fluids produced over the first several days of a cold is substantial and according to Turner et al ("Efficacy of tremacamra, a soluble intercellular adhesion molecule 1, for experimental rhinovirus infection: a randomized clinical trial." JAMA 281.19 (1999): 1797-1804) the amount of expelled fluids from the anterior nares is approximately 33 g over 7 days for an adult cold. In addition to these fluids secreted from the nostrils, a significant volume of secreted fluids may be swallowed. Overall, during a cold, the high volume of secreted fluids would lead to dilution of any topical agent and its accelerated clearance, causing a significant reduction in the effective exposure time and effect in the nasal passages. Accordingly, one could reasonably conclude that the effective exposure time for any topical agent such as PVP-I during a cold might be no more than one or two minutes.

Another perceived limitation is that free iodine, the only active antimicrobial moiety in PVP-I solutions, is rapidly consumed by nasal mucous because of the presence of mucins, glycoproteins present in nasal mucous secretions that contain a high concentration of cysteine, which reacts readily with free iodine thereby inactivating it and making it unavailable for microbicidal action. Hill and Casewell (2000), previously referenced herein, demonstrated that nasal secretions reduced the microbicidal activity of 5% PVP-I cream and calculated that 1.0 mL of nasal secretions inactivated the equivalent of 22.5 mg of PVP-I. Given the volume of a solution that can be applied into the nasal passages and the likely concentration of PVP-I in such a solution, one would conclude that most if not all of the free iodine available for release from a PVP-I intranasal application could be inactivated by the nasal secretions. This problem is amplified during the common cold when the volume of secretions and the level of mucins are greatly elevated due to rhinorrhoea as discussed above. This is much less of a problem when PVP-I might be applied to the nasal passages for eradication of MRSA or other resident bacteria, where mucous is limited and rhinorrhoea is not typical.

Another long-standing perceived limitation is that PVP-I has significant toxicity for human cells. Kramer et al (2002), previously referenced herein, showed that a PVP-I concentration of 2.5% or greater was toxic to the nasal cilia and therefore generally unsuitable for use in the nose. A concentration of 1.25% or lower did not cause ciliotoxicity. However, even at or below 1.25%, PVP-I has significant toxicity for human immune cells particularly relevant to the treatment of the common cold. Van den Broek et al ("Interaction of povidone-iodine compounds, phagocytic cells, and microorganisms." Antimicrobial Agents and Chemotherapy 22.4 (1982): 593-597) showed that PVP-I significantly reduced the viability of granulocytes at concentrations above 0.05%, with virtually all granulocytes destroyed above 0.1%. Because granulocytes play a central role in the cellular immune processes that eliminate viruses during a cold, such toxicity generally would be considered undesirable for a cold treatment agent. Monocytes, which have an important immune signalling role in a cold and act in concert with granulocytes to eliminate viruses, showed slightly more resilience to PVP-I, but were substantially degraded by PVP-I concentrations above 0.1%. Because the toxicity of PVP-I to immune cells has been known in the art since 1982, it has presented a long-standing perceived barrier to the development of PVP-I for many therapeutic applications. Again and in contrast, this is much less of a problem when PVP-I is applied to the nasal passages for eradication of resident bacteria, where immune cells are not actively engaged in fighting an infection.

In an effort to combat the cellular toxicity problem of aqueous PVP-I preparations and expand the utility of PVP-I, researchers recently have sought to develop liposomal formulations of PVP-I wherein the majority of the PVP-I is encapsulated in liposomes. Such liposomal PVP-I preparations have significantly reduced toxicity to human cells, potentially making them more suitable for certain intranasal applications, but not the common cold. While trapping the majority of the PVP-I within liposomes reduces toxicity, it also slows the rate and/or extent of free iodine release, which also reduces its potency such that, and as further described herein, renders it unsuitable for an application such as the common cold and such liposomal PVP-I formulations have never been proposed for the treatment or prevention of the common cold.

A further perceived limitation on the intranasal use of PVP-I is that iodine absorption could lead to systemic toxicity due to its well-known effects on thyroid function. It is well known in the art that the nasal passages represent a highly efficient portal for drugs and other agents to enter the systemic circulation. Therefore, when using any iodine-based product in the nasal passages, one needs to be extremely wary of the potential for excessive iodine absorption. In the United States, the National Institutes of Health guidelines state that the safe upper limit for total iodine ingestion by adults is 1,100 micrograms of iodine per day. This easily could be exceeded by intranasal applications of a PVP-I preparation in the nose depending on the volume, concentration and frequency of application of the preparation.

A final and crucial perceived limitation of PVP-I is that it is has limited activity against HRV, the virus responsible for the majority of colds. It is well known in the art that enveloped viruses are highly susceptible to inactivation by various agents including PVP-I, whereas non-enveloped or 'naked' viruses and particularly HRV, are resistant to inactivation by most chemical agents. A study by Reimer et al ("Antimicrobial effectiveness of povidone-iodine and consequences for new application areas." Dermatology 204.Suppl. 1 (2002): 114-120) showed that against the enveloped virus, human influenza virus, PVP-I at very low concentrations achieved a 4 $\log_{10}$ reduction in viable virus count, which is generally considered a microbicidal effect, within a 30 second exposure. This contrasts with human rhinovirus, a naked virus, where PVP-I at any concentration barely achieved a 1 log reduction after 30 seconds exposure and required 30 minutes exposure for a 4 log reduction. This further compares with another naked virus, adenovirus, where a 4 log reduction required only 5 minutes exposure, reinforcing the fact that rhinovirus is one of the most resilient naked viruses and further that activity of any agent against adenovirus or other naked viruses may not be representative of the agent's activity against HRV. Further, and in any case, adenovirus is not a common or recognised cause of the common cold and therefore not relevant for comparison in the context of the common cold.

The relatively weak activity of PVP-I against HRV has been corroborated by other studies. For example, Wutzler et al ("Virucidal activity and cytotoxicity of the liposomal formulation of povidone-iodine." Antiviral research 54.2 (2002): 89-97) showed that PVP-I produced a 1.1 log reduction in HRV after 30 seconds exposure and required 30 minutes for a microbicidal effect (4 log reduction), compared with a microbicidal effect after only 5 minutes for adenovirus and after only 30 seconds for the enveloped herpes simplex virus (HSV). Like adenovirus, HSV is not a common or recognised cause of colds.

Kawana et al ("Inactivation of human viruses by povidone-iodine in comparison with other antiseptics." Dermatology 195.Suppl. 2 (1997): 29-35) tested the activity of PVP-I against multiple viruses and confirmed the rapid microbicidal effect against enveloped viruses. However, PVP-I failed to produce a microbicidal effect against HRV within the maximum exposure period tested, which was 10 minutes. Given that these various studies were conducted under ideal in vitro conditions, one skilled in the art would assume that the performance of PVP-I against HRV in vivo, especially in the face of inactivation and clearance processes, would be clinically negligible. For all the above reasons, it would not be obvious that the intranasal application of PVP-I would be effective as a treatment for the common cold. Further, PVP-I has never been developed or commercialised as an intranasal treatment for the common cold and based on published information, has never been even assessed in a clinical study to determine its effectiveness as a prospective treatment for the common cold. If it were assessed in a controlled clinical study, those skilled in the art would assume that it would not meet the criteria for an effective treatment, namely that it would not cause a significant reduction in the severity of symptoms or the duration of a cold.

Despite all these limitations, the present inventors have surprisingly found that when used as an intranasal preparation according to the methods of the present invention, PVP-I is effective in reducing both the severity of symptoms of a cold and the duration of a cold. Further, it has additional benefits with respect to reducing the viral load and viral shedding in the nasal passages during a cold, reducing secondary illnesses, and reducing the risk or severity of serious LRI and exacerbations in at-risk individuals. Finally, methods are disclosed that have utility in prevention of colds.

SUMMARY OF THE INVENTION

The present invention involves methods for the treatment and prevention of the common cold, including certain sequelae and secondary illnesses, where the causative or potentially causative agent of the common cold is a virus. In all cases, the methods involve the application at ambient temperature of pharmaceutical preparations to the nasal passages of human subjects, said preparations comprising at least 0.10% w/v and no more than 2.5% w/v PVP-I and where at least 50% of the PVP-I is not associated with liposomes or other particulate carriers.

Accordingly in one aspect, the present invention provides a method of treating the common cold in a human subject caused or potentially caused by a virus, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of reducing the activity, viability or number of viruses within the nasal passages of a human subject, wherein the viruses are causative or potentially causative agents of the common cold, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of reducing the symptoms of the common cold in a human subject caused or potentially caused by a virus, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of reducing the duration of the common cold in a human subject caused or potentially caused by a virus, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of reducing the risk, incidence or severity of a secondary illness associated with the common cold in a human subject caused or potentially caused by a virus, wherein the secondary illness is selected from the group consisting of bronchitis, otitis media and sinusitis, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of reducing the risk, incidence or severity of lower respiratory illness associated with the common cold caused or potentially caused by a virus and in human subjects who suffer from COPD, asthma, emphysema or cystic fibrosis, or individuals with compromised immunity, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers.

In another aspect the present invention provides a method of preventing or reducing the risk of transmission of the common cold from a human subject with symptoms of the common cold to uninfected human subjects, the method comprising applying to the nasal passages of the human subject with cold symptoms, at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers and wherein the causative or potentially causative agent of the common cold is a virus.

In another aspect the present invention provides a method of avoiding the common cold in a human subject who has been exposed to others with common cold symptoms, the method comprising applying to the nasal passages of the human subject at ambient temperature, an effective amount of a pharmaceutical preparation comprising povidone-iodine (PVP-I) at a concentration of between 0.10% and 2.5% w/v and in which at least 50% of the PVP-I is not associated with liposomes or other particulate carriers and wherein the causative or potentially causative agent of the common cold is a virus.

BRIEF DESCRIPTION OF THE DRAWINGS

FIG. 1 is a graph derived from a mathematical model of an HRV infection of the nasal passages, and shows the predicted viral load over time during a typical common cold for untreated subjects and those treated with intranasal PVP-I commencing at 24 hours after first symptoms and according to the preferred treatment method.

FIG. 2 is a graph showing the projected symptom severity scores from the mathematical model as a function of time for untreated subjects and those treated with intranasal PVP-I commencing at 24 hours after first symptoms and according to the preferred treatment method.

FIGS. 3 to 6 are graphs showing the actual results for each of 4 subjects with colds who were treated with intranasal PVP-I according to the preferred method. Each of the graphs shows the symptom severity measured as Total Symptom Scores (TSS) as reported at each scoring event over 4 days for each of the 4 subjects with typical cold symptoms compared with typical mean daily TSS results for untreated patients as reported in published studies where a placebo control arm was used.

FIG. 7 is a graph showing the mean daily TSS results for the above 4 subjects compared with typical mean daily TSS results for untreated patients as reported in published studies where a placebo control arm was used.

FIGS. 8 to 11 are graphs showing the TSS results for 4 colds experienced by 2 subjects when subjects commenced treatment with PVP-I at the first signs of a cold, rather than 24 hours after first symptoms as in FIGS. 3 to 7.

FIG. 12 is a graph showing the mean daily TSS results for the 4 colds from FIGS. 8 to 11 compared with typical mean daily TSS results for untreated patients as reported in published studies where a placebo control arm was used.

FIG. 13 is a graph showing the mean daily TSS results when treatment commenced at first symptoms compared with treatment commencing at 24 hours after first symptoms and further compared with typical mean daily TSS results over a similar time period for untreated patients as reported in published studies where a placebo control arm was used.

DEFINITIONS

In this patent specification, adjectives such as first and second, left and right, front and back, top and bottom, etc., are used solely to define one element or method step from another element or method step without necessarily requiring a specific relative position or sequence that is described by the adjectives. The terms "comprises," "comprising," "includes," "including," or similar terms are intended to mean a non-exclusive inclusion, such that a method, system or apparatus that comprises a list of elements does not include those elements solely, but may well include other elements not listed.

Unless defined otherwise, all technical and scientific terms used herein have the same meaning as would be commonly understood by those of ordinary skill in the art(s) to which this invention belongs.

As used herein, the terms "common cold" or "cold(s)" refers to an infection of the nasal passages as defined herein that causes local and systemic symptoms, the constellation of which is generally defined as the common cold. This definition excludes secondary illness such as bronchitis, sinusitis and otitis media.

As used herein, "free iodine" refers to that elemental or diatomic iodine which is in solution and not actually bound to the polymer, in the case of povidone-iodine, although it may initially have been so bound. The free iodine concentration represents the instantaneous microbicidal potency of the iodophor solution and is measured according to methods taught in U.S. Pat. No. 3,028,300 to Cantor, incorporated herein by this reference.

As used herein, "available iodine" refers to that iodine of the iodophor which is ultimately available to be released from the polymer as free iodine. It therefore includes free iodine in solution, diatomic iodine available from tri-iodide ions as well as diatomic iodine held within a reservoir formed by the polymer structure. The available iodine does not include iodide ions. Available iodine is measured by thiosulfate titration in accordance with United States and British Pharmacopeia monographs.

As used herein, "total iodine" refers to all forms of iodine including free iodine, available iodine, iodide, iodate and other charged species of iodine in solution.

As used herein, "effective amount" refers to the dosage volume and frequency of the administration of a pharmaceutical preparation containing PVP-I according to the inventive method, which is sufficient to be effective in the application. The effective amount will vary in a manner which would be understood by a person of skill in the art with patient age, sex, weight, nasal passage volume etc. An appropriate dosage and dosage frequency can be ascertained through routine trial.

As used herein, "PVP-I NS" refers to a pharmaceutical preparation containing PVP-I for intranasal use as broadly defined by the present invention, or when used in relation to the specific examples cited, refers to a 0.25% PVP-I nasal spray prepared as described in the examples.

As used herein, "ambient temperature" refers to the temperature in the environment at which the method of the current invention is conducted. Typically ambient temperature will be about 10° C. to about 30° C. Importantly the term "ambient temperature" means that neither the pharmaceutical preparation nor the nasal passages of the subject to be treated are exposed to external heating in carrying out the method of the present invention.

"Viral shedding" refers to the amount or concentration of virus present in nasal washings or other nasal sampling technique. As used herein, the term is generally equivalent to the term "viral load" and "Extracellular Viral Load" or "EVL", each of which terms refers to the concentration or amount of virus in the nasal passages during a cold.

As used herein, the term "liposome" has the normal meaning in the art, while "particulate carriers" means liposomes, microspheres, nanoparticles, Large Porous Particles (LPP) or laser-pulse polymer coated molecule preparations as generally defined, used and referenced in WO 99/60998 by Fleischer et al. As used herein, the term "liposomal PVP-I" or "liposomal PVP-I preparations" refers to all preparations containing PVP-I where the PVP-I is predominantly entrapped in liposomes or other particulate carriers. Conversely, the term "non-liposomal PVP-I" or "non-liposomal PVP-I preparations" refers to preparations of PVP-I where the majority of the PVP-I is not entrapped, encapsulated or otherwise bound to liposomes or other particulate carriers.

DETAILED DESCRIPTION OF THE INVENTION

The present invention comprises methods for the treatment and prevention of the common cold and sequelae, the methods in all cases employing application to the nasal passages of human subjects of non-liposomal PVP-I preparations at ambient temperature where the concentration of PVP-I is between 0.10% and 2.5% w/v. The inventive methods produce substantial positive outcomes in key clinical measures of the common cold, including reducing the severity of symptoms and the duration of a cold and thereby constitute methods for the effective treatment of the common cold.

The inventive methods further provide benefits in terms of reduced incidence, risk or severity of common secondary illnesses, such as sinusitis, bronchitis and otitis media. The methods further provide benefits in terms of reduced incidence, risk or severity of serious LRI and disease exacerbations in at-risk patient populations. The methods further provide benefits in terms of reduced viral shedding from the nasal passages and thereby reduced risk of transmission of the cold to family members and others. The methods further provide benefits in terms of avoiding acquiring the common cold when subjects are exposed to colds from other people.

The present discovery that non-liposomal PVP-I preparations can be effective in treating and preventing colds has been made in spite of all the limitations known in the art and previously outlined herein, which in the absence of the present disclosures would not lead one skilled in the art to conclude that PVP-I preparations as disclosed might be safe and effective in such applications.

One inventive step leading to this discovery by the present inventors was the creation by them of a mathematical model of the course of a typical cold caused by HRV. This model, referred to herein as the "HRV model" is further elaborated in Example 1. The HRV model integrates assumptions, data and relationships about and between numerous variables affecting the viral load and cold symptoms during a cold caused by HRV and thereby provides a prediction of viral load and symptoms of a typical HRV cold over the time course of an HRV cold. The HRV model further integrates and incorporates the effect of PVP-I preparations applied to the nasal passages according to the inventive method and enables prediction of the effect of such application on viral load and symptoms over the time course of a cold.

Using the HRV model, the present inventors have discovered that while PVP-I may have relatively weak activity against HRV, and further that any such effect may be significantly depreciated by inactivation and clearance, when used according to the inventive method, PVP-I can be effective in significantly reducing the HRV viral load in the nasal passages. Further, this reduction surprisingly leads to a significant reduction of cold symptoms and cold duration. Given that HRV is the most resistant known virus to the action of PVP-I, the predicted activity against HRV by the model would indicate that the inventive methods would be at least as effective in treating colds caused by other more sensitive viruses.

Based on the data previously referenced by Wutzler et al (2002) and Reimer et al (2002), under ideal in vitro conditions, one could expect that non-liposomal PVP-I preparations at suitable concentrations for use in the nasal passages would produce approximately a 1.6 log reduction (97.5% reduction) in HRV viral load in two minutes, which is a reasonable approximation of the time for exposure of the virus to PVP-I given clearance effects during a cold. Further, allowing for depreciation of that performance due to inactivation by mucins and organic material in the nose, including viruses and cells, a net percent reduction in viral load after each application can be estimated. For example, if the depreciative effect of inactivation is 50%, then the effective reduction in HRV viral load with each PVP-I application drops to 38.8%; if the depreciative effect is further increased to 80%, then the effective reduction in HRV viral load drops to 19.5%. However, according to the model and with a suitable frequency of application, even a viral load reduction of 19.5% after each application would degrade the viral load sufficiently over the course of the cold to cause a significant reduction in viral shedding, the severity of cold symptoms and the duration of the cold. This surprising result is due to a combination of factors integrated into the model including the low efficiency of cell infection and re-infection by HRV, the fact that a critical number of HRV virus particles is needed to initiate and perpetuate an infection, the relatively long infection cycle for HRV and the frequency of repeated applications of the PVP-I preparation.

The model also surprisingly predicts that regardless of whether the PVP-I preparation according to the inventive method is first introduced at 24 hours, 48 hours or 72 hours after first symptoms, the method produces a subsequent substantial reduction in symptoms and cold duration. Thus the use of PVP-I as a treatment for the common cold would not be encumbered by the short intervention window generally considered a barrier or limitation for any cold treatment.

The present inventors verified the outcomes predicted by the HRV model and the effectiveness of inventive method in treating the common cold by pilot clinical test results as further described in Examples 2 and 4. Example 2 showed that in people who had confirmed colds for at least 24 hours prior to treatment, a PVP-I preparation according to the inventive method is effective in treating HRV colds and colds caused by other viruses, as measured by a reduction in total symptom scores (TSS) and cold duration or Time to Alleviation of Illness (TAI). Example 4 showed that in people who had the first signs of a cold, a PVP-I preparation according to the inventive method is effective in reducing TSS by more than 90% overall and in preventing cold symptoms reaching a level where they would otherwise impair the person's daily activities.

While viral load was not directly assessed in the studies, given that the primary mode of action of PVP-I is based on the destruction of virus by free iodine as predicted by the HRV model, it reasonably must be concluded that the activity, viability and/or number of viruses in the nasal passages would be reduced and thereby viral shedding from the nose would be reduced.

Further, by suppressing the viral load and shortening the period during which virus is present in the nasal passages and reducing cold symptoms especially mucous secretions, the inventive methods would reduce the incidence or severity of secondary illness, such as bronchitis, otitis media and sinusitis. This is because the reduced viral load and mucous secretions would reduce the risk of migration of significant amounts of infectious viruses to secondary locations such as the bronchi, middle ear and sinuses, respectively. Examples 2, 3 and 4 provide further evidence of this effect.

Similarly, by suppressing the viral load, shortening the period during which virus is present in the nasal passages and reducing mucous secretions, the inventive methods would reduce the risk and/or severity of serious LRI and/or exacerbations of underlying respiratory diseases in at-risk individuals.

Similarly, by suppressing the viral load, shortening the period during which virus is present in the nasal passages and reducing mucous secretions, the inventive methods would reduce the risk of transmission of the virus from infected individuals to other people.

The inventive methods are also effective in preventing or avoiding colds in people who have not yet acquired a cold but are exposed to others with cold symptoms. In relation to prevention of colds, some of the considerations pertinent to treatment do not apply. Notably, the purpose of the intervention with the PVP-I preparation is not principally to reduce the viral load and interrupt the infection cycle thereby shortening the duration of colds, nor principally to remove immunogenic stimulators and thereby reduce local and systemic symptoms of a cold. Rather, it is to destroy cold viruses in the nasal passages before they have the opportunity to infect nasal cells or to destroy cold viruses after their release during early cycles of cell infection before cold symptoms first appear or to destroy cold viruses at the first signs of a cold and before cold symptoms have a chance to fully develop. As described in Example 3, PVP-I preparations according to the inventive method, and when used after an individual is exposed or may have been exposed to a cold, reduced the incidence of significant colds by approximately 88% over an 18 month period. Further as shown in Example 4, PVP-I preparations according to the inventive method, and when used after an individual first detects cold symptoms, prevented colds from flourishing and eliminated the impairment typically associated with cold symptoms.

In addition to the predicted direct effects of the inventive PVP-I preparations in degrading the viral load during a cold, and without wishing to be bound by any specific theoretical explanations, the present inventors believe that the surprising, favourable outcomes observed in treating and preventing the common cold may be due to the propitious and unexpected interaction of several other mechanisms of action that in some cases augment or complement the direct effects of PVP-I, or in other cases, and despite their apparent limiting effect theoretically, may operate surprisingly favourably in practice to contribute to effectiveness of PVP-I in treating colds. The combination and interaction of these other mechanisms as an explanation for the effectiveness of PVP-I in any illness has not previously been disclosed.

By way of example, and again without wishing to be bound by any specific theoretical explanations, the observed utility of intranasal PVP-I in treating colds, may be due in part to the effects of PVP-I on viral receptor proteins on the surface of nasal cells and those proteins on the surface of viruses that are essential for viral attachment and entry into cells. As disclosed recently by Sriwilaijaroen et al ("Mechanisms of the action of povidone-iodine against human and avian influenza A viruses: its effects on hemagglutination and sialidase activities." Virology Journal 6.1 (2009): 124), PVP-I can block the attachment of influenza virus to human cells by altering the binding proteins on the virus and/or on the receptor proteins on the cell surface. While influenza virus is the known cause of only a small percentage of colds, it is likely that similar effects would occur with respect to HRV and other cold viruses. This effect could further explain and contribute to the observed utility of PVP-I in treating colds and may also contribute to its effectiveness in preventing colds.

By way of further example and again without wishing to be bound by any specific theoretical explanations, the observed utility of PVP-I in treating colds, may be due in part to the fact that free iodine interacts with many proteins and likely would damage and/or inactivate immune signalling proteins in the nasal mucous. Konig et al ("Effects of Betaisodona® on parameters of host defense." Dermatology 195.Suppl. 2 (1997): 42-48) demonstrated that PVP-I inactivated the cytokine TNF-a after its release from immune cells. U.S. Pat. No. 8,303,994 to Kessler et al discloses that free iodine interfered with the binding between *Staph aureus* enterotoxin and T-cells causing the T-cells to stop releasing cytokines. This possible effect could further explain and contribute to the observed utility of PVP-I in treating colds.

By way of further example and again without wishing to be bound by any specific theoretical explanations, the observed utility of PVP-I in treating colds may be because of the toxicity of PVP-I against monocytes and granulocytes, and that this feature, rather than a limitation, may surprisingly contribute favourably to the efficacious outcomes observed in treating colds with PVP-I according to the inventive method. This is because, by eliminating these cells, PVP-I stops the propagation and amplification of systemic symptoms that otherwise would be caused by the release of cytokines from these cells. By way of further explanation, because the direct impact of PVP-I on viral load as predicted by the HRV model would be so profound over the course of a cold, the normal role of the immune cells in eliminating the viruses becomes largely redundant in the treatment of the condition and their elimination by the toxic effects of PVP-I, when imposed in the HRV model, has negligible impact on the course of the infection or symptoms when using PVP-I according to the inventive method.

There are several aspects of the invention now outlined that represent important components of the inventive methods. One important aspect of the present invention is that the PVP-I preparation according to the inventive method is a non-liposomal PVP-I preparation as defined herein. This is contrary to current thought in the art that espouses the use of liposomal PVP-I preparations for intranasal uses such as eradication of MRSA colonies, because of their reduced toxicity, prolonged action and improved tolerability, as further described in Wutzler et al (2002) and Gluck et al (2007), both previously referenced herein. Liposomal PVP-I preparations are more fully described by Reimer et al ("Povidone-iodine liposomes an overview." Dermatology 195.Suppl. 2 (1997): 93-99) and typically entail the encapsulation of the majority of the PVP-I in a preparation in a multilaminar or unilaminar vesicle. This and other references cited herein suggest that these properties may be useful in preventing or treating infections of the eye, preventing infections in wounds and eradicating antibiotic-resistant bacteria from nasal passages, in all cases where prolonged residence and antimicrobial effect in conjunction with low toxicity and high tolerability may be important.

In liposomal PVP-I preparations, the vast majority of the PVP-I is encapsulated in a liposome and a small proportion of the PVP-I and/or free iodine is outside the liposome in aqueous solution and in a form of equilibrium with the PVP-I and/or free iodine inside the liposome. However, only the free iodine outside the liposome is available for interaction with microorganisms. This two-phase system (liposomal-aqueous) ensures a relatively low level of active agent outside the liposome, which is consistent with its reduced toxicity. PVP is inert and known to have no appreciable toxicity, so the only toxicity in PVP-I preparations, whether liposomal or non-liposomal, arises from free iodine. Therefore, it would be obvious to one skilled in the art that the reduced toxicity of liposomal PVP-I preparations compared with non-liposomal PVP-I preparations must be largely due to very low free iodine levels outside the liposome. This is further evidenced by the reduced antimicrobial properties of liposomal PVP-I preparations compared with aqueous PVP-I preparations, given that only free iodine has any antimicrobial properties.

It is evident that the liposomal two-phase system retards the release of PVP-I and/or free iodine, thereby providing for prolonged release over time and longer duration of action in the absence of other factors. The system also necessarily reduces the rate and/or quantum of replenishment of PVP-I and/or free iodine into the aqueous phase in response to depletion of free iodine by antimicrobial action and inactivation, as would occur during a cold. Accordingly, liposomal PVP-I preparations are generally not suited to the treatment of colds due to the low instantaneous levels of free iodine and the slow replenishment rate from the liposomal phase, which countervails the need for rapid action and high instantaneous potency during a cold, especially in the face of free iodine inactivation and rapid clearance.

Further, liposomal PVP-I preparations are less effective against HRV. Wutzler et al (2002), previously referenced, compared liposomal and non-liposomal PVP-I preparations for activity against HRV. After a 30 second exposure, the aqueous PVP-I preparation produced a 1.1 log reduction (92% reduction) in virus compared with only a 0.2 log reduction (37% reduction) for the liposomal PVP-I preparation based on the same concentration of PVP-I. After a 2-minute exposure, which is likely approaching the longest exposure time that could be achieved during a cold, the reductions were 1.6 log (97.5%) and 0.6 log (75%) respectively. However, these tests were conducted under ideal in vitro conditions. During a cold, in the liposomal PVP-I preparation, the small amount of active agent outside the liposome would be subject to rapid inactivation and dilution, and therefore would be expected to have a negligible direct effect on HRV viral load in vivo. Because of the slow replenishment of active agent outside the liposomal phase, any prolonged effect would be countervailed by rapid clearance and further inactivation. In summary, in the case of a cold, a more rapidly and aggressively acting agent is essential and the benefits of liposomal PVP-I preparations, i.e. reduced toxicity and longer duration of action, work against the desired outcomes in the treatment of the common cold. Therefore, the current invention strongly prefers that the PVP-I preparation is a non-liposomal preparation, where the majority of the PVP-I is not entrapped in liposomes, and all subsequent references to PVP-I preparations, formulations or solutions herein, unless otherwise specified, refer to non-liposomal PVP-I preparations.

Another aspect of the present invention is that the PVP-I concentration in the PVP-I preparation should be greater than 0.10% w/v to effect the most rapid and potent action during a cold, especially given inactivation and clearance considerations. It is known in the art that the free iodine concentration in PVP-I solutions paradoxically increases as the concentration of PVP-I is reduced from 10% to approximately 0.2%. The reason for this is that as a PVP-I solution is diluted, the free iodine dissociates from the polymer-iodine complex and is released into solution, thereby increasing the free iodine level and reducing the amount of available iodine that remains bound to the polymer. In this regard, Atemnkeng et al ("Comparison of free and bound iodine and iodide species as a function of the dilution of three commercial povidone-iodine formulations and their microbicidal activity." International Journal of Pharmaceutics 317.2 (2006): 161-166) found that at PVP-I concentrations below 0.10% the available iodine is greatly depleted. As the PVP-I concentration is reduced below 0.05%, the majority of the available iodine is unbound from the complex and in the form of free iodine, such that the solution effectively becomes an aqueous iodine solution and any reservoir effect of PVP-I is eliminated for all practical purposes. In all cases, those in the art would conclude that for a PVP-I preparation to be effective and to effectively constitute a PVP-I solution rather than a predominantly iodine solution, the majority of the free iodine needs to be bound to the polymer with only a small minority of the free iodine in solution.

As further reported by Atemnkeng in the above cited reference, the highest free iodine levels occurred when the PVP-I concentration was between 0.1% and 0.5%. On this consideration, PVP-I concentrations between above 0.1% and less than 1.0% are preferred, and concentrations between 0.2% and 0.5% are most preferred.

The effect of intranasal agents on ciliated epithelium in the nose is an important consideration around the use of a PVP-I preparation in the nose, because any ciliotoxicity can be detrimental to normal mucociliary clearance function and any agent that causes ciliotoxicity may be deemed unsuitable for general or widespread use. Reimer et al (2002), previously referenced herein, note that PVP-I solutions containing 2.5% or higher concentrations of PVP-I were ciliotoxic causing a complete loss of ciliary function. However, a concentration of 1.25% or lower was not ciliotoxic. On this consideration, the composition for nasal use should be a PVP-I concentration of less than 2.5% and preferably less than or equivalent to 1.25%.

With respect to the intranasal tolerability of PVP-I, as distinct from ciliotoxicity, the present inventors have discovered that when the concentration of PVP-I in aqueous preparations is greater than 1.0%, the preparation may be irritating to the nasal mucosa in some individuals and not suitable for repeated, frequent and general use, as would be required in the effective treatment or prevention of the common cold. On this consideration, a preferred composition for nasal use is a concentration of PVP-I at or below 1.0%.

A limitation previously identified that could affect the safety and utility of any PVP-I solution for intranasal use, especially in the treatment and prevention of the common cold, is the likelihood of iodine absorption and potential for excessive iodine uptake, with consequent elevated serum iodine levels and unwanted effects on thyroid function, especially in those people who have thyroid disease. In the United States, the National Institutes of Health guidelines state that the safe upper limit for iodine ingestion by adults is 1,100 micrograms of iodine per day. According to the methods of the present invention, a 0.6 mL dose delivered four times daily to an adult, would reach this upper limit when the PVP-I concentration was 0.5%. However, the systemic bioavailability of the iodine available from a PVP-I preparation is likely to be significantly lower than the levels indicated by such a calculation. The iodine moiety principally absorbed and of concern with respect serum iodine levels and thyroid function, is the iodide ion. In the treatment of the common cold where significant viral and other protein material is present, especially the glycoprotein mucin, a significant proportion of any free iodine released from PVP-I would become irreversibly bound to proteins and not available for conversion to iodide ion or subsequent uptake into the bloodstream through nasal mucous membranes. Therefore, even at 1.0% PVP-I concentration, it is unlikely that iodide uptake would reach or exceed the safe daily limit. However, in a highly preferred embodiment, the PVP-I concentration for intranasal use would contain less than 0.5% PVP-I.

A final aspect of the present invention is that the application of the PVP-I preparation to the nasal passages occurs without the adjunctive or external use of heat to the nasal passages. Rhinothermy is a process recently popularised for treating colds that involves the application of heated and humidified air to the nasal passages. As reported by Aroll ("Non-antibiotic treatments for upper-respiratory tract infections (common cold)." Respiratory Medicine 99.12 (2005): 1477-1484), rhinothermy without adjunctive use of a microbicide can be effective in treating colds. PVP-I preparations are heat labile and the heating of the environment in which PVP-I preparations are applied may lead to instability of the preparation, especially causing unpredictable or elevated instantaneous free iodine levels and otherwise increase the risk of allergic, toxic or other local reactions on the nasal mucosa. It could also lead to enhanced iodine absorption, systemic toxicity and other unwanted effects. Therefore, an aspect of the present invention is that the application takes place at ambient temperatures, especially below 100° F., and without the use of external or adjunctive heating.

In summary, the present invention recognises and concludes that the surprising positive treatment effects of PVP-I on the common cold as outlined in Examples 1, 2, 3 and 4, may be the outcome of the combination of several propitious actions including (a) the degradation of the activity, viability and/or number of viruses in the nasal passages to interrupt the infection cycle and remove the immunogenic stimulators of the immune response as described Example 1, (b) the direct disruption of the cellular immune response by the reduction of the viability of immune cells, and (c) inhibition of viral attachment to target cells through denaturation or alteration of binding proteins on cells or viruses. There may be other effects, not described herein, that further contribute to the observed effectiveness of PVP-I in treating colds.

Further, the present invention recognises that liposomal PVP-I preparations are unsuitable for use in the treatment of the common cold and strongly prefers non-liposomal PVP-I preparations. Further, the present invention recognises that the concentration of the PVP-I must be greater than 0.10% for the solution to effectively constitute a PVP-I solution and to have sufficient antimicrobial capacity to be effective in the treatment or prevention of the common cold. Further, the present invention recognises that due to safety, tolerability and ciliotoxicity considerations, the concentration of PVP-I in the preparation should be less than 2.5%, preferably less than or equal to 1.0% and more preferably less than or equal to 0.5%.

Prior art discloses methods for using certain iodine or PVP-I based preparations for treating or preventing certain respiratory conditions, but only some address the use of PVP-I in the treatment or prevention of the common cold, and none of these discloses or anticipates the inventive methods disclosed herein.

U.S. Pat. No. 6,171,611 to Picciano, incorporated herein by this reference, discloses an iodine nasal solution and method for preventing and/or treating sinusitis and related conditions by applying the solution to the nostrils of affected patients. This reference does not disclose the use of PVP-I, nor does it disclose the treatment or prevention of the common cold.

United States Patent Application Publication No. 2006/0280809 by Leshchiner et al., incorporated herein by this reference discloses that PVP-I can be used to treat ear and nasal infections, and to that end claims pharmaceutical compositions containing between 5% and 50% PVP-I combined with certain excipients, especially oils, and certain vehicles, especially glycosaminoglycans. There is no disclosure of the treatment or prevention of the common cold with PVP-I and the proposed PVP-I concentrations are outside the range of the present invention and known to be toxic in the nasal passages.

United States Patent Application Publication No. 2010/0203166 by Rezakhany, incorporated herein by this reference, discloses methods for inhibiting respiratory infections by agitating or gargling an oral rinse or mouthwash in the throat and allowing vapours to penetrate the nasal passages, wherein iodine may be an ingredient in the oral rinse solution. It does not refer to any composition utilising PVP-I nor any intranasal method for treating or preventing the common cold.

U.S. Pat. No. 5,038,769 to Krauser, incorporated herein by this reference, discloses a method and apparatus for treating the common cold that involves the application of air heated to above 100° F. to the nasal passages followed by a microbicidal agent in a nasal spray, where the microbicide could comprise a 0.5% PVP-I solution. The method disclosed in all cases requires the prerequisite and concomitant application of heated air to the nasal passages. The use of a PVP-I preparation at ambient temperature without the application of heated air is not disclosed.

U.S. Pat. No. 7,297,344 by Fleischer et al, incorporated herein by this reference, discloses liposomal PVP-I preparations for use in the nasal passages and identifies one highly preferred use as "the local treatment of infections of the nose, mouth and throat" with specific examples including herpes simplex virus infections and opportunistic infections associated with immune deficiency states such as HIV and after organ transplantation, acute and chronic laryngopharyngitis, angina, and tissue repair applications especially in functional and cosmetic tissue remodelling. Methods for treating or preventing the common cold are not disclosed, nor is the use of PVP-I preparations other than liposomal PVP-I preparations.

U.S. Pat. No. 6,694,041 and associated application US 2003/0180380 Al to Hansen, incorporated herein by this reference, disclose a method for treating or preventing the common cold by using a nasal spray comprising an iodine solution in combination with certain salts. In all cases, the patent specifies the use of iodine in combination with other halogen salts or zinc gluconate and based on context and exemplifications, the "iodine" refers to total iodine and especially iodide, rather than free iodine. While PVP-I is disclosed as a possible source of some of the iodine, the exemplified preparations contain less than 0.05% PVP-I and therefore constitute iodine solutions rather than solutions of PVP-I, and would be ineffective in treating or preventing the common cold and are outside the concentration range disclosed in the current invention. This patent provides only a suggestion of the use of PVP-I for the treatment of the common cold but especially given the exemplifications it would not lead one skilled in the art to the currently claimed invention.

In summary, the present invention describes methods for the treatment and prevention of the common cold, which are not disclosed or anticipated by the prior art.

Accordingly in a first aspect the present invention provides a method of treating the common cold in a human subject, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus.

In a second aspect the present invention provides a method of reducing the activity, viability or number of viruses within the nasal passages of a human subject, wherein the viruses are causative or potentially causative agents of the common cold, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers.

In a third aspect the present invention provides a method of reducing the symptoms of the common cold in a human subject, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus.

In a fourth aspect the present invention provides a method of reducing the duration of the common cold in a human subject, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus.

In a fifth aspect the present invention provides a method of reducing the risk, incidence or severity of a secondary illness associated with the common cold in a human subject, wherein the secondary illness is selected from the group consisting of bronchitis, otitis media and sinusitis, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus. This aspect is premised on the discovery that the method will reduce the volume of mucous secreted, reduce the activity, viability or number of cold viruses contained in secreted mucous, and reduce the period during which microbe-laden mucous is present, which one skilled in the art would conclude will contribute to a reduced risk of viruses migrating to secondary sites in the respiratory tract to establish or contribute to secondary illnesses.

In a sixth aspect the present invention provides a method of reducing the risk, incidence or severity of lower respiratory illness associated with colds in human subjects who suffer from COPD, asthma, emphysema or cystic fibrosis, or individuals with compromised immunity, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus. This aspect is premised on the discovery that the method will reduce the severity and duration of the initial cold infection, which in itself would contribute to a reduced risk of exacerbation of underlying respiratory illnesses. In addition, and as with the fifth aspect, by reducing the volume of mucous secreted, the activity, viability or number of microorganisms in secreted mucous, and the period during which microbe-laden mucous is present, the method will contribute to a reduced risk of viruses migrating to the lower respiratory tract to establish a lower respiratory infection.

In a seventh aspect the present invention provides a method of preventing or reducing the risk of transmission of the common cold from a human subject with symptoms of the common cold to uninfected human subjects, the method comprising applying to the nasal passages of the human subject with cold symptoms, at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus. This aspect is premised on the discovery that the method will reduce viral shedding during a cold by reducing the volume of mucous secreted, the activity, viability or number of cold viruses shed in mucous, and the contagious period during which virus-laden mucous is present. It will also reduce transmission facilitating symptoms such as rhinorrhoea, sneezing, coughing and symptom-related activity such as nose blowing.

In an eighth aspect the present invention provides a method of avoiding or suppressing the common cold in a human subject who may not have cold symptoms but has been exposed to others with cold symptoms, the method comprising applying to the nasal passages of the human subject at ambient temperature, an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative or potentially causative agent of the common cold is a virus. This aspect is premised on the discovery that the method will sufficiently inactivate any cold viruses entering the nasal passages to prevent onset of the cold infection or that the method will eliminate or sufficiently inactivate cold viruses at an early stage in the infection process and thereby abort or significantly diminish the infection.

In a preferred embodiment, the concentration of PVP-I in the preparation is between about 0.1% and about 1.0% and more preferably between about 0.2% and about 0.5% and most preferably between about 0.2% and 0.45%.

In a preferred embodiment at least 70%, preferably at least 80%, more preferably at least 90% of the PVP-I is not associated with liposomes or other particulate carriers.

It is further preferred that the pharmaceutical preparation does not contain liposomes.

In a preferred embodiment the causative agent of the cold is selected from the group consisting of rhinoviruses, human coronaviruses, influenza viruses, human parainfluenza viruses, human respiratory syncytial viruses, adenoviruses, enteroviruses other than rhinoviruses, metapneumoviruses and any combinations thereof, and in particular rhinoviruses.

In another preferred embodiment the pharmaceutical preparation is administered into the nostrils of the human subject between 1 and 12 times daily with between about 50 µL and about 1000 µL of the pharmaceutical preparation administered to each nostril for each administration of the preparation.

In another preferred embodiment the common cold symptoms affected are typically selected from the group consisting of chills, headaches, aches and pain, tiredness, running nose, sneezing, cough, nasal congestion, sore throat and combinations thereof.

In another preferred embodiment, the pharmaceutical preparation may further comprise an agent selected from the group consisting of a decongestant, antihistamine, analgesic, antipyretic, anti-inflammatory, steroid, cough suppressant or cough expectorant.

In another preferred embodiment the pharmaceutical preparation may further comprise at least one pharmaceutically acceptable diluent, excipient or carrier. Typically, the pharmaceutically acceptable diluent or excipient is a flavour, sweetener, colouring agent, solvent, buffer, alcohol, polymer, surfactant or other diluent or excipient designed to optimize the nasal delivery, intranasal distribution, stability, effectiveness, acceptability, tolerability or other useful features of the preparation. In the event that liposomes or liposome-forming agents are included in the preparation, in all cases only a minority of the PVP-I in the preparation will be entrapped in the liposomes. One of ordinary skill in the art would be able to determine the appropriate types and quantities of carriers, diluents, or excipients to be used in the pharmaceutical preparation for intranasal use as required by the method.

In another preferred embodiment the pharmaceutical preparation is in a dosage form selected from the group consisting of intranasal solutions, drops, sprays, gels, aerosols, or inhalants, but may include any other device or formulation suitable for administering an effective amount of the PVP-I to the nasal passages.

In order that the nature of the present invention may be more clearly understood preferred forms thereof will now be described with reference to the following non-limiting examples.

EXAMPLE 1

In order to verify and elucidate the benefits of the inventive method as well as establish the optimum dosage frequency and duration of treatment for a PVP-I nasal preparation according to the inventive method, the present inventors created a mathematical model of a typical common cold infection caused by HRV, using variables and assumptions derived from published information about HRV infections of the nasal passages and symptomatology of the common cold. The model is referred in the present invention as the "HRV model" and predicts the extracellular viral load (EVL) over time from the moment of first infection through the following nine days, which encompasses the typical total duration of a HRV cold. The HRV model incorporated assumptions about the replication rate and infection cycle of HRV, based on published data, as well as assumptions about the number of viruses in the initial inoculum, cell re-infection rates, the number of viruses released from each infected cell and the timing and impact of the immune response on viral load. The list of variables incorporated into the model is shown in Table 1.

TABLE 1

Summary of Variables in HRV Model

| Variable | Description |
| --- | --- |
| Virions in initial inoculum | Number of viruses in the initial infection |
| Virus infection rate | % of viruses in EVL that actually infect cells |
| Virions released per lysed cell | Number of new viruses released from each infected cell when it ruptures |
| Cell infection rate ceiling | Max number of cells that can be infected per hour |
| Cell total infection ceiling | Max number of cells that can be infected in total |
| Cell infection cycle (hours) | Number of hours from cell infection to rupture |
| Cell rupture timing | % of infected cells at any time that rupture each hour from 8-14 hours after first infection |
| Immune response delay | Delay from infection to start of immune response and attendant symptoms |
| Immune system effect on EVL | Rate at which the immune system reduces EVL |

The model was calibrated by comparing the pattern of viral load projections from the model with the typical pattern of viral load for HRV infections based on data from four clinical studies where the viral load was measured over time after subjects were deliberately infected with HRV. These studies, incorporated herein by reference, are: Schiff G. et al, "Clinical Activity of Pleconaril in an Experimentally Induced Coxsackievirus A21 Respiratory Infection" Journal of Infectious Diseases, 2000, 181:20-26; Hayden, F., et al. "Efficacy and safety of oral pleconaril for treatment of colds due to picornaviruses in adults: results of 2 double-blind, randomized, placebo-controlled trials" Clinical Infectious Diseases 36.12 (2003): 1523-1532; Gem J. et al, "Inhibition of Rhinovirus Replication In Vitro and In Vivo by Acid-Buffered Saline" Journal of Infectious Diseases, 2007, 195: 1137-1143; Turner R. et al, "Efficacy of Tremacamra, a Soluble Intercellular Adhesion Molecule 1, for Experimental Rhinovirus Infection: A randomized Clinical Trial" JAMA, 1999, Vol 281, No 19, pp 1797-1804.

In addition to predicting EVL over the normal course of a HRV infection, the model was designed to predict the severity of overall cold symptoms based on the known relationship between EVL and symptoms from published data. Symptom scores predicted by the model were calibrated by comparing the pattern of symptom score projections from the model with the typical pattern of symptom scores for HRV infections based on data from two clinical studies where the symptoms were assessed in conjunction with HRV viral load (Schiff et al, 2000; Hayden et al, 2003, both referenced above).

The expected effects of a PVP-I preparation as defined in the present invention were then imposed on the HRV model based on the known capability of PVP-I to reduce the viral load of HRV, the likely exposure time of virus to PVP-I in the nasal passages during a cold, the depreciative effect of inactivation on PVP-I performance, and applying different daily dosage frequencies, durations of treatment, and three different delays before treatment commenced after first symptoms, namely 24 hours, 48 hours and 72 hours. The model predicted that PVP-I would have a rapid and significant impact on EVL, symptoms and cold duration regardless of whether the PVP-I was used 24, 48 or 72 hours after first symptoms. Clearly, the earlier the PVP-I intervention, the shorter the total duration of the cold, but unlike antiviral drugs which suffer from a limited window of time after first symptoms in which they must be used, the HRV model surprisingly predicted no similar constraint with PVP-I in that, even if first used 72 hours after first symptoms, PVP-I caused a rapid decline in EVL and consequently in projected symptom severity compared with untreated colds.

Model projections for EVL and symptoms based on a typical set of model assumptions are shown in FIG. 1 and FIG. 2. Only the data for treatment commencing at 24 hours after first symptoms are shown in FIGS. 1 and 2, because a 24 hour delay is considered to reflect the expected normal and practical delay in commencement of treatment after a subject first noticed cold symptoms. FIG. 1 shows the projected viral load in the nose as a function of time for subjects treated with PVP-I at 24 hours after first symptoms and approximately 4 times daily thereafter, compared with typical viral load (EVL) data for untreated subjects.

As shown in FIG. 1, the HRV model projected an initial decline in viral load followed by a "saw tooth" pattern reflecting the immediate degradation of the EVL after each application followed by a series of viral regrowth episodes as new viruses were released from infected cells in between PVP-I applications. According to the HRV model, by application of PVP-I at 24 hours after first symptoms of a cold, the growth in the EVL could be interrupted, the EVL would remain suppressed and then would shrink to close to zero and nasal shedding effectively would cease within 3 days. This compares with up to 3 weeks of ongoing shedding for untreated HRV colds.

The projected symptom severity chart is shown in FIG. 2. The HRV model predicted that by preventing the initial peak in EVL and repeatedly degrading the remaining EVL, PVP-I would rapidly reduce symptom severity compared with untreated colds and if used at 24 hours after first symptoms, would shrink the total duration of colds from an average of 7 days after commencement of treatment to as few as 2-3 days.

Alternative dosage schedules to the four times daily dosage were assessed in the HRV model including longer treatment schedules and a more aggressive initial treatment regimen of initial hourly applications of the PVP-I nasal spray followed by 4 times daily application. Treatment with schedules longer than 5 days appeared to offer little benefit according to the HRV model. However, the more aggressive initial hourly treatment predicted a slightly more rapid outcome in terms of resolution of symptoms.

EXAMPLE 2

An experiment was undertaken by using a commercially-available PVP-I preparation containing 7.5% PVP-I. The nasal spray preparation for the experiment was prepared by using 0.67 mL of the commercial preparation and mixing this with 20 mL of saline (approximately 1:30 dilution) to yield 0.25% PVP-I in a standard decongestant-type nasal spray bottle with a capacity of approximately 25 mL that delivered approximately 100 µL per pump action. In the context of this experiment, this pharmaceutical preparation may be referred to as "PVP-I NS".

Four adults known to the inventors who were otherwise healthy and who had recently caught colds agreed to participate. Three of the people had colds that occurred in the spring or the autumn, so it was highly likely that they were caused by HRV. The fourth person had caught their cold during winter and it presented with more severe initial symptoms than is typical of HRV colds and for both reasons therefore was likely caused by coronavirus, influenza virus or RSV. Two of the suspected HRV cold subjects, were instructed to spray three shots (approximately 300 µL) per nostril four times a day for four days. The third HRV person was instructed to use the same dosage of PVP-I NS hourly for the first four hours followed by four times daily for a total of four days. The person with the suspected non-HRV cold was similarly instructed to use the PVP-I NS hourly for the first four hours followed by four times daily for a total of four days.

Everyone started treatment approximately 24 hours after they first noticed cold symptoms. Participants completed a daily symptom diary and reported on five local symptoms (runny nose, cough, sneezing, congestion, sore throat) and three systemic cold symptoms (malaise, headache, and chills), in accordance with published and accepted methods (Jackson, G., et al. "Transmission of the common cold to volunteers under controlled conditions: I. The common cold as a clinical entity." AMA archives of internal medicine 101.2 (1958): 267-278). Symptoms were reported just prior to each dosage of PVP-I NS during the four days of treatment and then on the morning of the fifth day.

Although the present study was not a placebo controlled clinical trial, there are published data available for placebo results from controlled and blinded common cold studies which provide a useful guide to comparative performance. In this case, the placebo/untreated data were derived from Eccles et al ("Efficacy and safety of an antiviral Iota-Carrageenan nasal spray: a randomized, double-blind, placebo-controlled exploratory study in volunteers with early symptoms of the common cold." Respiratory Research 11 (2010): 108) with adjustments for differences in scoring methodologies.

Key measures of product performance used in the experiment were: (a) Total Symptom Scores (TSS) calculated as the mean daily sum of the symptom scores for the eight local and systemic symptoms, and (b) Time to Alleviation of Illness (TAI), determined by the time in days to reach a point where runny nose was absent and no other symptom scored higher than "mild" in terms of severity. TSS has been used in some cold treatment studies as the primary endpoint for establishment of treatment efficacy, including a published study of carrageenan nasal spray as a cold treatment as described by Eccles et al (2010) referenced above. Time to Alleviation of Illness was used as the primary endpoint in the phase III common cold study for the antiviral drug, pleconaril, as described by Hayden et al (2003) previously referenced herein.

For subject 1, TSS increased initially on the first day of treatment but rapidly declined by the end of the first day and was significantly reduced by the end of day 2 compared with day 1. By day 3, virtually all symptoms were resolved. For subject 2, TSS dropped to around half the initial level by the end of day 2 and virtually all symptoms were resolved by day 4, although there was an ongoing non-impairing level of symptomatology for another two days. For subject 3, on the more aggressive treatment schedule, the TSS dropped dramatically by the end of fourth hour of treatment and all significant symptoms had resolved by the end of the second day. For subject 4, on the more aggressive treatment schedule and with the suspected non-HRV cold, the cold symptoms were initially not responsive to treatment, with TSS increasing significantly on the first day of treatment. However, by the end of the second day, TSS had fallen to 25% of the peak TSS level and by the end of the third day symptoms were almost fully resolved.

All participants found the treatment acceptable and none reported side effects, local irritation or other concerns. All indicated that they believed the PVP-I nasal spray was effective in rapidly resolving their colds compared with their expectations about how their colds would have normally progressed otherwise. Further, none of the participants suffered from a secondary illness subsequent to their cold, including sinusitis, otitis media or bronchitis.

Graphs showing the TSS results as reported by each subject during the course of the study are shown in FIGS. 3-6. These data show a consistent pattern for the three suspected HRV colds, although the reduction in cold symptoms was significantly faster in the case of subject 3 where the more aggressive treatment schedule was adopted. The data for subject 4 suggest a more resistant infection, which did not initially respond to treatment on day 1, but by the end of day 2 was non-impairing and thereafter quickly resolved. This is consistent with many non-HRV colds which can have more severe and intractable symptoms than HRV colds.

FIG. 7 and Table 2 show the mean daily TSS for each of the four subjects compared with typical untreated mean daily TSS data compiled from published studies. These data show that PVP-I NS was effective in reducing cold symptoms compared with published data for untreated colds, with an average 57% reduction in mean daily TSS by day 2 of treatment compared with typical untreated symptom scores and virtually all symptoms resolved by day 3 or 4, compared with up to eight days for untreated colds.

TABLE 2

Mean Daily TSS Reduction with PVP-I NS

| | Prior to PVP-I | Mean daily TSS by Day of Treatment | | | | |
|---|---|---|---|---|---|---|
| | | 1 | 2 | 3 | 4 | 5 |
| Subject 1 | 10.4 | 8.4 | 4.4 | 2.6 | 0.0 | 0.0 |
| Subject 2 | 9.7 | 6.7 | 4.8 | 4.0 | 3.0 | 1.0 |
| Subject 3 | 11.2 | 5.0 | 2.5 | 0.8 | 0.0 | 0.0 |
| Subject 4 | 6.0 | 10.0 | 8.8 | 3.0 | 1.3 | 0.5 |
| Average | 9.3 | 7.5 | 5.1 | 2.6 | 1.1 | 0.4 |
| Untreated (placebo) | 9.3 | 10.8 | 11.8 | 12.1 | 10.6 | 8.7 |
| Average % reduction in symptoms versus untreated | | −30% | −57% | −78% | −90% | −96% |

The TSS data were compared with those reported for carrageenan nasal spray with standardising adjustments for the different scoring methods. In the carrageenan study reported by Eccles et al (2010) already referenced herein, the authors used the sum of the TSS for days 2, 3 and 4 as their primary endpoint and against this, carrageenan nasal spray delivered an overall reduction in symptom severity of approximately 25% versus placebo. Against the same endpoint, the reduction in symptom severity with PVP-I NS in the present study was 74%.

While TSS is a useful measure for comparing treatments, it is not considered a valid clinical endpoint by some regulatory authorities, because it is an un-weighted composite of scores for eight different symptoms. A more valid measure is thought to be the Time to Alleviation of Illness (TAI), i.e. cold duration, which was the primary endpoint in the pleconaril phase three study described by Hayden et al (2003), referenced previously herein. In the current study, the PVP-I NS resolved cold symptoms in 2.3 days on average compared with 6.3 days for pleconaril and 7.3 days for placebo, a difference of 5.0 days or a 68% reduction in cold duration for PVP-I NS compared with placebo.

Overall, the results obtained in the study indicate that intranasal PVP-I is effective in the treatment of the common cold. Further, the pattern of the treatment effects on the suspected HRV colds as shown in FIGS. 3-5 are generally consistent with the predictions of the HRV model and support the proposition that PVP-I works in part by the degradation of the EVL to interrupt the infection cycle and remove the immunogenic stimulators of the immune response. In addition, the overall dramatic reduction in symptoms and abrupt shortening of cold duration, including for subject 4 after day 1, may be consistent with other PVP-I effects including the disruption of the immune response by the reduction of the viability of immune cells and/or denaturation of signalling proteins such as cytokines and/or inhibition of viral attachment to target cells through denaturation or alteration of binding or receptor proteins.

EXAMPLE 3

One adult male person know to the inventors evaluated the performance of using PVP-I NS preventatively as a method of avoiding colds over an eighteen month period. The individual normally experienced up to six significant colds each year, where a "significant" cold was considered to be one where the symptoms led to impairment of daily activities and otherwise met the criteria for a common cold. This person used a PVP-I NS for 18 months, including two winters, a period when overall he normally would have experienced a total of at least eight colds.

He used the same PVP-I NS preparation as employed in the treatment experiment in Example 2. He was instructed to use the product only when he encountered someone at home, work, traveling or elsewhere who exhibited cold symptoms such as runny nose, sneezing or coughing. He was instructed to use the PVP-I NS twice daily for five days after each encounter. The person was provided with a supply of the commercial 7.5% PVP-I preparation, saline solution and a supply of empty 25 mL nasal spray bottles. After each such encounter with a suspected cold sufferer, the person prepared approximately 20 mL of the PVP-I NS by diluting the PVP-I preparation 1:30 with saline and pouring the diluted solution into a clean 25 mL nasal spray bottle. The freshly prepared solution was then used twice daily for five days after the encounter. At the end of each five day period, the diluted PVP-I NS in the nasal spray device was discarded and the device cleaned. During the period he was instructed to note any cold symptoms he experienced.

At the end of the study period, the person reported that he had experienced only one significant cold during the 18 month period and had experienced no instances of secondary illnesses including bronchitis, sinusitis or otitis media, despite typically suffering from bronchitis or sinusitis as sequelae of colds in the past. In the one instance of a significant cold, during the three days prior to first noticing cold symptoms he had not observed or noted any encounter with another person with cold symptoms and therefore had not been using the PVP-I NS. However, he reported that within 12 hours after noticing his cold symptoms he commenced using the PVP-I NS four times daily and the cold resolved within a few days and caused only moderate impairment of daily activities for approximately one or two days only. These results were consistent with the results in Example 2. The user believed that the use of the PVP-I NS greatly reduced his risk of acquiring a cold during the treatment period and to the extent that one cold did occur, the symptoms were greatly ameliorated and no secondary illness occurred.

Although a single person case, this study supports the proposition that twice daily or more frequent use of PVP-I NS after encountering someone with cold symptoms will help the person avoid catching a cold and reduce the incidence or severity of colds for the person. However, such a regimen is unlikely to avoid or prevent all colds in a user because one is not always aware of the presence of cold viruses. Accordingly, one could unknowingly touch a contaminated surface or breathe in contaminated aerosol without actually observing another person with obvious cold symptoms. It appears that this occurred in the single instance of a significant cold that was observed during the study period. This example also supports the claim that use of the inventive method will reduce the risk, incidence or severity of secondary illnesses associated with the common cold, such as bronchitis, otitis media and sinusitis.

EXAMPLE 4

An experiment was undertaken using the PVP-I NS preparation as described in Example 2. Two adults known to the inventors and who were regular cold sufferers agreed to participate in the experiment designed to test the effectiveness of PVP-I nasal spray in reducing or preventing cold symptoms when applied at the first signs of a cold, in contrast to the experiment reported in Example 2, where subjects were required to wait 24 hours after first symptoms before commencing treatment. The subjects are hereafter referred to as Subject 1 and Subject 2.

The study was conducted over one year. At any time during that period if either subject started to experience symptoms of a cold and were convinced the symptoms were those of a cold, they were instructed to prepare and start using PVP-I NS. After the first application, they were instructed to apply the product four times a day for a total of five days, or a total of approximately 20 applications. However, some flexibility was allowed in the actual frequency and number of the applications in this case. Unlike Example 2, Subjects were asked to use the product for five days rather than four, because they would be starting effectively a day earlier in the overall symptom cycle. Unlike Example 2, subjects were asked to continue reporting symptoms for two days after completion of the five-day treatment or a total of seven days. In all other material respects, the protocol and reporting were the same as the experiment reported in Example 2.

The hypothesis tested in this experiment was that if the HRV model described in Example 1 is valid, then application of PVP-I NS at the first signs of a cold, which is typically approximately 24 hours after viral infection starts in the nasal passages, should suppress the viral load before the infection has had a chance to flourish and in so doing would (a) prevent the cold symptom complex from fully developing and (b) more significantly reduce overall cold symptoms, compared with starting PVP-I NS treatment 24 hours after first symptoms, as in Example 2, when the infection and cold symptoms are already flourishing and the symptom complex close to full development.

TSS was used as the primary endpoint. Unlike Example 2, TAI was not measurable, because due to the PVP-I NS treatment, in no case did the illness symptoms reach a point that could be used as a benchmark for effective measurement of alleviation of illness. One benchmark that was found useful in this case for assessing severity of illness was whether or not the illness reached an impairing level, which for the purposes of the experiment was defined as a TSS greater than 4.

Subject 1 contracted only one cold during the period while Subject 2 experienced three. All four colds occurred during non-winter months (two in autumn, two in spring) indicating the causative virus probably was HRV in all cases. FIGS. 8-11 show the TSS data as reported by the two subjects for the four colds. Each TSS data point was based on symptom diary reports at each specific time, typically immediately before each PVP-I NS application. In each case, the down arrows indicate the approximate time of each PVP-I NS application.

Subject 1: For Subject 1/cold 1, hereafter referred to as S1/1, the person used the nasal spray for a total of 21 applications over the five days. The PVP-I NS application almost immediately suppressed symptoms to a non-impairing level, i.e., a TSS score of 4 or less. However, symptoms rose to above the impairing level on day 5 before rapidly declining, with the cold completely resolved at the end of day 7 and without recurrence of symptoms thereafter.

Subject 2: The second subject experienced three colds, referred to hereafter as S2/1, S2/2 and S2/3 with TSS results as shown in FIGS. 9, 10 and 11 respectively. For S2/1, as shown in FIG. 9, the person used 20 applications over the five days and applied the product four times daily. In this case, the symptoms, while perceptible throughout the first four days never rose to an impairing level and disappeared on day 5. The subject stated they knew they had a cold during the five days, but symptoms remained at a low level and at no stage impaired their daily activities.

For S2/2, as shown in FIG. 10, the person also applied PVP-I NS 20 times over 5 days although the frequency was less consistent than S1/1 or S2/1. Because their cold symptoms first appeared late afternoon on the first day, they applied the treatment twice on that day and six times the following day. By the morning of day 3 the subject was convinced that they had no cold and consequently reduced applications to once daily. Surprisingly, on the morning of day 5, which was 58 hours after symptoms were last observed, mild local symptoms (sneezing, rhinorrhoea, congestion) returned, at which time the subject applied the PVP-I NS treatment hourly for four hours and the symptoms promptly disappeared again. Symptoms then reappeared the next morning (congestion, rhinorrhoea), so the subject again used the PVP-I NS treatment hourly for three hours and symptoms finally disappeared without recurrence. Again, PVP-I NS suppressed symptoms to a non-impairing level throughout the course of the cold.

For S2/3 as shown in FIG. 11, the subject applied PVP-I NS 17 times over 5 days. Symptoms disappeared after approximately 48 hours, but like S2/2 re-emerged on several occasions over the next few days, each time resolving, in this case after only a single application of PVP-I NS.

In this experiment, TAI (time to alleviation of illness) assessments were not possible, because the PVP-I NS intervention mostly prevented the symptom complex from fully developing in the first instance. Only one case (S2/3) had symptomatology that met the criteria for "illness" as defined by the TAI endpoint (rhinorrhoea plus any other symptom greater than mild), so measuring alleviation of illness was impossible for all practical purposes. In none of the four cases did subjects experience any secondary illness such as bronchitis, sinusitis or otitis media, and none reported any sensitivity reactions, stinging or other intolerance to the PVP-I NS preparation.

FIG. 12 and Table 3 show the mean daily TSS for each of the four subjects compared with typical untreated mean daily TSS data compiled and extrapolated from published studies, notably Eccles et al (2010) already referenced herein. These data show that PVP-I NS was overall effective in treating colds when used at the first signs of a cold, with an average 89% reduction in mean daily TSS by day 2 of treatment compared with typical untreated symptom scores and virtually all symptoms resolved by day 3 or 4, compared with up to eight days for untreated colds.

TABLE 3

Mean Daily TSS using PVP-I NS, 0-Hour Start of Treatment

| | Mean TSS by Day of Symptoms | | | | | | |
|---|---|---|---|---|---|---|---|
| | 1 | 2 | 3 | 4 | 5 | 6 | 7 |
| S1/1 | 1.4 | 1.5 | 2.1 | 2.9 | 5 | 2.4 | 0.8 |
| S2/1 | 0.7 | 1.4 | 0.8 | 1.1 | 0.4 | 0 | 0 |
| S2/2 | 2.9 | 0.3 | 0 | 0.6 | 0.6 | 0 | 0 |
| S2/3 | 4.2 | 1.4 | 0.8 | 0 | 0.2 | 0.2 | 0 |
| Average PVP-I NS | 2.3 | 1.1 | 0.9 | 1.2 | 1.5 | 0.6 | 0.2 |
| Untreated (placebo) | 7.8 | 11 | 12 | 12 | 11 | 8.7 | 7.4 |
| Average % reduction in symptoms Vs untreated | −71% | −89% | −92% | −90% | −86% | −93% | −97% |

FIG. 13 shows the comparative average mean daily TSS data for Examples 2 and 4. On an area-under-the-curve (AUC) basis, the AUC difference over the eight days after start of treatment was 77% when treatment started 24 hours after first symptoms, compared 92% for the same eight-day period when treatment started at the first onset of symptoms.

This experiment demonstrates several important features of the invention. Firstly, it provides further evidence of the effectiveness of the inventive method, notably the aspect of avoiding or suppressing the common cold in people who have been exposed to cold viruses and not yet experienced symptoms or as specifically assessed in this example, had the first signs of that a cold was developing. Secondly, the improved effectiveness of PVP-I NS when used at the first signs of a cold compared with its use 24 hours after first symptoms is consistent with the HRV Model in Example 1. Thirdly, the fact that symptoms often returned after cessation or a reduction in frequency of treatment with PVP-I NS points to the importance of the frequency of application and other aspects of the inventive method. Fourthly, it demonstrated the effectiveness of the method in preventing secondary illnesses such as bronchitis, sinusitis and otitis media.

Advantages of the Invention

Despite nearly half a century of research, there is no effective treatment or preventative available for the common cold. The common cold remains the most prevalent disease afflicting humankind and every year leads to massive morbidity, personal suffering, hospitalisations, loss of productivity, medical system burden and costs, and contributes to the global crisis of increasing antibiotic resistance. The present invention discloses novel methods that employ PVP-I for intranasal use, which are demonstrably safe and effective in treating colds as measured by reduction of cold symptoms and shortening of the overall duration of cold symptoms, as well as preventing colds.

The methods possess industrial applicability for the preparation of a commercial product for the treatment and prevention of the common cold. A commercial product based on the invention could be made readily available at relatively low cost and for the first time would provide a product to effectively treat and prevent colds and significantly reduce the number of presentations of colds to doctors, thereby alleviating the burden on the doctors and freeing their time to address the growing needs of ageing populations worldwide. Moreover, it would reduce the costs to patients or governments associated with payment or reimbursement for such consultations. Moreover, it would greatly reduce the prescribing of antibiotics for colds and associated secondary illnesses such as bronchitis, otitis media and sinusitis, thereby not only further reducing patient and reimbursement costs, but importantly, making a significant contribution to reduced antibiotic resistance and allowing precious antibiotics to be reserved for serious bacterial diseases. Moreover, it would reduce the risk, cost, morbidity, suffering and hospitalization associated with serious lower respiratory tract illness and exacerbations that occur as sequelae of colds in susceptible individuals such as those with asthma, cystic fibrosis, emphysema and COPD and those with compromised immunity. Finally, it would reduce the productivity losses and overall morbidity and suffering associated with colds in the general population and potentially for the first time bring to heel the most prevalent disease afflicting humankind.

The effectiveness of the methods disclosed for both treatment and prevention does not depend on the particular organism or genetic or antigenic makeup of the organism causing or potentially causing the infections. The methods do not cause side effects, are well tolerated, and with respect to treatment of colds, can be used together with conventional therapeutic or palliative measures for colds, such as antihistamines, decongestants, analgesics, cough medicines, and other medications to further enhance the effectiveness of the methods.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognised that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognise that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

The invention claimed is:

1. A method of treating the common cold in a human subject in need thereof, the method comprising applying to the nasal passages of the human subject at ambient temperature of between 10° C. to 30° C., an effective amount of a pharmaceutical preparation comprising povidone-iodine (PVP-I) at a concentration of greater than 0.10% w/v and less than about 1.25% w/v and in which at least 50% of the PVP-I is not associated with liposomes or other particulate carriers and wherein the causative agent of the common cold is a virus selected from the group consisting of rhinoviruses, human coronaviruses, human parainfluenza viruses, human respiratory syncytial viruses, adenoviruses, enteroviruses other than rhinoviruses, metapneumoviruses, and any combinations thereof.

2. The method according to claim 1, wherein the PVP-I concentration in the pharmaceutical preparation applied to the nasal passages is 0.1% to about 1.0% w/v.

3. The method according to claim 2, wherein the PVP-I concentration in the pharmaceutical preparation applied to the nasal passages is about 0.2% to about 0.45% w/v.

4. The method according to claim 1, wherein the pharmaceutical preparation does not contain liposomes.

5. The method according to claim 1, wherein the pharmaceutical preparation is administered into the nostrils of the human subject, between 1 and 12 times daily.

6. The method according to claim 1, wherein the causative agent of the common cold is a rhinovirus.

7. A method of reducing the symptoms of the common cold in a human subject in need thereof, the method comprising applying to the nasal passages of the human subject at ambient temperature of between 10° C. to 30° C., an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers and wherein the causative agent of the common cold is a virus selected from the group consisting of rhinoviruses, human coronaviruses, human parainfluenza viruses, human respiratory syncytial viruses, adenoviruses, enteroviruses other than rhinoviruses, metapneumoviruses, and any combinations thereof.

8. The method according to claim 7, wherein the PVP-I concentration in the pharmaceutical preparation applied to the nasal passages is 0.1% to about 1.0% w/v.

9. The method according to claim 8, wherein the PVP-I concentration in the pharmaceutical preparation applied to the nasal passages is about 0.2% to about 0.45% w/v.

10. The method according to claim 7, wherein the pharmaceutical preparation does not contain liposomes.

11. The method according to claim 7, wherein the pharmaceutical preparation is administered into the nostrils of the human subject, between 1 and 12 times daily.

12. The method according to claim 7, wherein the causative agent of the common cold is a rhinovirus.

13. The method according to claim 7 where the common cold symptom is selected from the group consisting of chills, headaches, aches and pain, tiredness, running nose, sneezing, cough, nasal congestion, sore throat and combinations thereof.

14. A method of reducing the activity, viability or number of viruses within the nasal passages of a human subject in need thereof, wherein the viruses are causative agents of the common cold, the method comprising applying to the nasal passages of the human subject at ambient temperature of between 10° C. to 30° C., an effective amount of a pharmaceutical preparation comprising povidone-iodine (PVP-I) at a concentration of greater than 0.10% w/v and less than about 2.5% w/v and in which at least 50% of the PVP-I is not associated with liposomes or other particulate carriers, wherein the virus selected from the group consisting of rhinoviruses, human coronaviruses, human parainfluenza viruses, human respiratory syncytial viruses, adenoviruses, enteroviruses other than rhinoviruses, metapneumoviruses, and any combinations thereof.

15. The method according to claim 14, wherein the PVP-I concentration in the pharmaceutical preparation applied to the nasal passages is 0.1% to about 1.0% w/v.

16. The method according to claim 15, wherein the PVP-I concentration in the pharmaceutical preparation applied to the nasal passages is about 0.2% to about 0.45% w/v.

17. The method according to claim 14, wherein the pharmaceutical preparation does not contain liposomes.

18. The method according to claim 14, wherein the pharmaceutical preparation is administered into the nostrils of the human subject, between 1 and 12 times daily.

19. The method according to claim 14, wherein the virus is a rhinovirus.

\* \* \* \* \*